United States Patent
Stephenson et al.

(10) Patent No.: US 10,350,361 B2
(45) Date of Patent: Jul. 16, 2019

(54) FLUID DELIVERY PEN WITH FINAL DOSE STOP AND IMPROVED DOSE SETTING FEATURES

(71) Applicant: WOCKHARDT LIMITED, Aurangabad, Maharashtra (IN)

(72) Inventors: Matthew Stephenson, Dannevirke (NZ); Barry Knight, Weybridge (AU); Stephen Knowles, London (GB); Umesh Joshi, Aurangabad (IN); Ashok Tyagi, Aurangabad (IN)

(73) Assignee: WOCKHARDT LIMITED, Aurangabad (IN)

(*) Notice: Subject to any disclaimer, the term of this patent is extended or adjusted under 35 U.S.C. 154(b) by 234 days.

(21) Appl. No.: 15/128,103

(22) PCT Filed: Mar. 13, 2015

(86) PCT No.: PCT/IB2015/051843
§ 371 (c)(1),
(2) Date: Sep. 21, 2016

(87) PCT Pub. No.: WO2015/145294
PCT Pub. Date: Oct. 1, 2015

(65) Prior Publication Data
US 2018/0169345 A1  Jun. 21, 2018

(30) Foreign Application Priority Data
Mar. 25, 2014  (IN) .......................... 1008/MUM/2014

(51) Int. Cl.
*A61M 5/315* (2006.01)
*A61M 5/24* (2006.01)

(52) U.S. Cl.
CPC .......... *A61M 5/31551* (2013.01); *A61M 5/24* (2013.01); *A61M 5/31541* (2013.01);
(Continued)

(58) Field of Classification Search
CPC .......... A61M 5/31551; A61M 5/31541; A61M 2205/581; A61M 5/31585;
(Continued)

(56) References Cited

U.S. PATENT DOCUMENTS 6,004,297 A    12/1999  Steenfeldt-Jensen et al.
7,771,398 B2   8/2010   Knight et al.
(Continued)

FOREIGN PATENT DOCUMENTS

CH    703 993 A2    3/2012
EP    0 608 343 B1  12/1997
(Continued)

*Primary Examiner* — Emily L Schmidt
(74) *Attorney, Agent, or Firm* — Maschoff Brennan

(57) ABSTRACT

The fluid delivery pen of the present invention has a reduced dose setting friction mechanism which may produce a sound of higher audibility for each click corresponding to one unit dose set using a dose setting mechanism and also produces a sound of lower audibility than the former for each click when the set dose is reduced using the dose setting mechanism. The fluid delivery pen driving mechanism of the present invention has an indication to an end of dose of fluid in a cartridge.

20 Claims, 28 Drawing Sheets

(52) U.S. Cl.
CPC ......... *A61M 5/3156* (2013.01); *A61M 5/3158* (2013.01); *A61M 2205/581* (2013.01)

(58) Field of Classification Search
CPC ............ A61M 5/31553; A61M 5/3156; A61M 5/31583; A61M 5/3155
See application file for complete search history.

(56) References Cited

U.S. PATENT DOCUMENTS

| | | |
|---|---|---|
| 2008/0108953 A1 | 5/2008 | Moser et al. |
| 2008/0243087 A1 | 10/2008 | Enggaard et al. |
| 2008/0287883 A1 | 11/2008 | Radmer et al. |
| 2009/0137964 A1 | 5/2009 | Enggaard et al. |
| 2009/0240195 A1 | 9/2009 | Schrul et al. |
| 2009/0254047 A1 | 10/2009 | Thogersen et al. |
| 2009/0275916 A1 | 11/2009 | Harms et al. |
| 2009/0299297 A1 | 12/2009 | Möller et al. |
| 2010/0094205 A1* | 4/2010 | Boyd ................ A61M 5/31595 604/68 |
| 2010/0145282 A1 | 6/2010 | Hansen et al. |
| 2010/0324494 A1 | 12/2010 | Plumptre |
| 2011/0034878 A1 | 2/2011 | Radmer et al. |
| 2012/0053516 A1* | 3/2012 | Cronenberg ........ A61M 5/2033 604/82 |
| 2015/0051551 A1 | 2/2015 | Hirschel et al. |

FOREIGN PATENT DOCUMENTS

| | | |
|---|---|---|
| EP | 1 003 581 B1 | 11/2000 |
| EP | 1 681 070 A1 | 7/2006 |
| WO | 2005/018721 A1 | 3/2005 |

* cited by examiner

FLUID DELIVERY PEN WITH FINAL DOSE STOP AND IMPROVED DOSE SETTING FEATURES

FIELD OF INVENTION

The present invention relates to fluid delivery disposable pen for the delivery of fluids into persons in need thereof. In particular this invention is related to devices, for the delivery of fluid into patients. These devices are multi-dose delivery disposable devices, where a pre-selected quantity of fluids can be delivered into patients. The fluid delivery pen comprises a dose setting mechanism and a driving mechanism. The fluid delivery pen of the present invention has a reduced dose setting friction mechanism which may produce a sound of higher audibility for each click corresponding to one unit dose set using a dose setting mechanism and also produces a sound of lower audibility than the former for each click when the set dose is reduced using the dose setting mechanism. The fluid delivery pen driving mechanism of the present invention has an indication to an end of dose of fluid in a cartridge. An end of dose mechanism of the present invention in a disposable fluid delivery pen does not make use of a component which is rotatable one or a separate movable non rotating member having threaded features. The devices of the present invention have the overall shape and appearance of a pen, and hence have been described as fluid delivery pen.

BACKGROUND OF THE INVENTION

Pen type drug delivery devices have application where regular injection by persons without formal medical training occurs. This is increasingly common among patients having diabetes where self injection of administration enables to conduct effective management of their disease.

In certain types of prior art medication delivery devices, such as fluid delivery pen type devices, cartridges of medication are used. The medication fluid to be used in the fluid delivery pen may be related to insulin regimen and varies from patient to patient and depends on the type of insulin to be injected (slow, medium, fast acting, or specific combinations of these), the lifestyle of the patient, the circumstances, patient's actual medical condition etc.

The prior art fluid delivery pen devices disclose piston rod or plunger rod whose engagement with a stopper or bunger of the cartridge facilitates the discharge of the medicament on its forward movement due to movement of the piston rod or the plunger rod on application of the force. The prior art fluid delivery pen devices with hollow piston rod having an internal thread have many advantages and is described in the U.S. Pat. No. 7,771,398 and referenced here with. A piston rod that has an internal non-locking helical thread can be substantially larger in diameter and will have a structurally efficient hollow cross section making it substantially stronger than an equivalent externally threaded rod. Further an injection device that has a direct mechanical drive between the person applying the injection force and the hollow piston rod being driven forward to inject the medicament. This ensures the person is aware of any problems in the dose delivery. The dose setting means as disclosed in (US '398) uses a bi-directional ratchet that produces tactile and auditory clicks when the outer dose-knob is rotated in order to set a dose. The audibility of dose setting means auditory clicks in (US '398) are uniform and same both when the dose is set and when the set dose is reduced.

Further the prior art hollow piston rod disposable fluid delivery pen are bigger in size. Further inner housing distal edge and the fluid cartridge holder or cartridge cover proximal edge are joined chemically or ultrasonically. Prior art hollow piston rod pen device may have external pen cap or pen lid orientation which may not be not only aesthetically presentable but also weak snap on feature to the fluid cartridge holder resulting in improper protection to the inner components. There may not be any audible click as the dose dial returns to "0". Shorter length and shape of the thumb pad/dose button may lead to incorrect dose of delivery.

In the case of patients who are old, infirm or physically impaired or having hearing impairment the only other way of recognizing or identifying the dose set is by visual indication through the magnifying lens the numerals displayed on the dose setting member. The prior art ascertainment of dose set by visual indication through magnifying lens falls short of expectation when such patients are also visually impaired. Hence there is a need to develop a mechanism by which when a dose set or a set dose is changed or reduced is recognizable by variation in the degree of sound of the clicking i.e. preferably of higher audibility when the dose is set and of relatively lower audibility when the dose is reduced. More so in the case of diabetic patients when the drug is insulin or insulin analogue which will have to be self administered too frequently in small doses accurately.

Further the prior art pen devices dose setting clicks are by means of unidirectional ratchets or occasionally bi-directional ones which produce uniform sound while the dose is being set or reduced or the dose is being delivered as in US 20110034878. The closest prior art dose setting mechanisms are enumerated below.

In EP 608 343 is described a fluid delivery pen having a dose setting mechanism wherein the dose is set by rotating a button relative to a housing to set a dose. The button is through a ratchet coupled to a driver, the ratchet forming a unidirectional coupling which during the rotation of the button in one direction to set a dose rides or clicks over the teeth of the ratchet. In U.S. Pat. No. 6,004,297 disclosure a pawl mechanism working between the driver tube and housing is used to produce click mechanism. In US 20090254047 a connector pipe 80, ratchet 100, protrusion 83 and track 101 combination perform the click sound. In US 20090299297 the shield 10 is axially slidable in the housing 30 but rotational locked to the housing 30 by the protrusion 11 sliding in the track 31. A rim of shield teeth 12 on the proximal end of the shield 10 interact with a corresponding rim of push button teeth 2 provided on the inside of the push button 1. In US 20080287883 a shield 60 is axially slidable mounted to the housing 10. The shield 60 is provided with a protrusion 61 sliding in a longitudinal track 12 provided on the inside surface of the housing 10. In US 20110034878 while the piston rod 307 moves axially to expel the set dose the tip 327 of the click finger 326 rides over the teeth 395 of the piston rod 307 being distributed between two consecutive larger teeth 396, thereby providing an audible feedback mechanism indicating to the user through audible clicks that the dosage is progressing.

The frictional reduction in all the prior art injection pen devices occurs when a user pushes on the push button (or injection button or dose button or thumb pad as they are known by various names), the force applied may be directed to the forward movement of the driving part and the frictional reduction may be brought about by forming a pivot bearing between the two parts. One of the means of reducing friction between the two components may be by minimizing the surface area of interaction between the two objects by virtue of which the radius of resulting friction force can be kept at a minimum.

Firstly these prior art fluid delivery pen devices disclose piston rod or plunger rod with an external thread whose engagement with a stopper or bunger of the cartridge facilitates the discharge of the medicament on its forward movement due to movement of the piston rod or the plunger rod on application of the force. Secondly, the thumb pad connection for an injection pen device which minimizes the forces a user most apply to inject a dose requires relative rotation to each other between the thumb pad and the mating component i.e. the driving part with which the thumb pad mates. The thumb pad connection to a fluid delivery pen device in some of the closest prior arts with a piston rod of external thread mechanism is enumerated below.

EP 1003581 discloses an injection device in which according to FIG. 15-16 comprises a scale drum, a bushing and a push button. The scale drum and bushing rotate together and the push button and bushing rotate relatively to each other. WO 2005/018721 discloses an injection device in which the push button is formed with a bore encompassing a stem on a sleeve member. The push button and the stem are welded together such that the push button and the sleeve member are axially and rotatably fixed to each other. US 20100145282 disclose an injection device in which at least one radial bearing between the push button and the protrusion is formed in the upper and lower area.

Unlike prior art fluid delivery pen devices with external threaded rods, minimization of the forces a user must apply to inject a dose achieved by frictional reduction when a user pushes on the thumb pad in prior art fluid delivery pen devices having hollow piston rod with an internal helical thread is still an unmet need more so as envisaged in the present invention having firstly an end of dose mechanism and secondly variable audibility features incorporated while dose setting or reduction of higher set dose.

Hence it is an objective of the present invention to address the various inadequacies in accurate dose setting and ease of dose delivery by patients having poor vision/hearing in the prior art fluid delivery disposable pen devices comprising a hollow piston rod with internal helical thread.

It is another objective of the present invention to have an end of dose mechanism in a fluid delivery disposable pen device comprising a hollow piston rod with internal helical thread.

Also it is an objective of the present invention to address this necessity of unmet need for frictional reduction which minimizes the forces a user must apply to inject a dose in a fluid delivery disposable pen device with a hollow piston rod with an internal thread having an end of fluid dose mechanism and variable audibility features while dose setting or reducing the dose set.

It may also be noted that in prior art fluid delivery pen devices that after repeated self administration of fluid, fluid runs low in the cartridge, and a user may attempt to set a dose that exceeds the amount of medication left in the cartridge. Further in certain other fluid delivery pen devices towards a better accuracy, a drug delivery device may be designed not to allow a user to dial a dose that is greater than the amount of medication remaining in the cartridge. In such fluid delivery pen devices there could be wastage of the fluid. Hence it may be necessary to avoid wastage of fluid in disposable fluid delivery pen device and the need to develop a mechanism wherein not only the entire fluid in the cartridge may be delivered (the remaining amount of the fluid in the cartridge to the practically allowable barest minimum) but also the dose setting mechanism may indicate the amount of fluid yet to be delivered when the last dose set is delivered. This may enable the user to set this dose and get it injected from a new fluid delivery disposable pen device. For example, when the last dose set in a disposable delivery device may be say 60 IU (International Units) of insulin, the amount of insulin remaining in the cartridge may be 50 IU, then an end of dose mechanism of the present invention may display 10 IU in the dose setting window after delivering 50 IU of insulin and by which the patient would still know that the balance 10 IU may have to be delivered.

The drug delivery pen device last dose lock-out mechanism or an end of the dose content mechanism have been reported in the prior arts in US20090275916, US20080243087, US2010324494, US2009137964, US20080108953 and US0090240195, the disclosures of which are incorporated herein by reference. These prior art devices necessarily have piston rod or plunger rod which have threads provided on their external surfaces.

US20090275916 discloses a dosing mechanism for a medication delivery device comprising a dose setting limiting mechanism with a dose limiting member. US20080243087 discloses an end of content mechanism which may be positioned in the space defined by the inner walls of a driver wherein an outer surface of driver may be directly coupled to the inner surface of a drum scale of an injection device. US20100324494 discloses a dose setting mechanism which comprises a rotatable shaft having a first pitch in the first portion and a second pitch in the second portion of the rotatable shaft. US 20090137964 discloses an injection device comprising a track coupled to one of the housing or the dose setting member. US20080108953 discloses an injection device comprising different threaded rods and internal thread including several contact faces. US20090240195 discloses a lock for an injection device including a threaded rod, wherein the lock includes one of an anti-rotation or claw-type securing element.

It may be observed that all of the above prior art fluid delivery pen devices having an end-of-content mechanism comprises an external threaded plunger or piston rod which engages with the stopper or bunger of the cartridge for dispensing the medicament. It may further be observed that the above prior art devices makes use of either an existing rotatable or a moving member or a separate component for achieving the last dose lock out mechanism. For example in US20090275916, a dose limiting member, in US20080243087, a limiter coupled to the driver, in US US20100324494, a last dose lock-out mechanism comprises a rotatable shaft and a non-rotating member, In US 20090137964, a nut member, In US US20080108953 and US20090240195, a rotating sleeve.

SUMMARY OF THE INVENTION

It may be one of the aspects of the invention that the fluid delivery pen may have a dose setting mechanism by which when a dose set or a set dose is changed i.e. increased or reduced may be recognizable by variation in the degree of sound of the clicking i.e. preferably of higher audibility when the dose is set and of relatively lower audibility when the dose is reduced.

It may be another aspect of the invention that the fluid delivery pen have a final dose stop mechanism to avoid wastage of fluid by ensuring not only the entire fluid in the cartridge may be delivered (i.e. the remaining amount of the fluid in the cartridge to the practically allowable barest minimum) but also by the indication of dose setting mechanism the amount of fluid yet to be delivered may be inferred when the last dose or final dose set is delivered. This may enable the user to set this dose and get it injected from a new fluid delivery disposable pen device. By the final dose stop mechanism may be meant no further fluid would be left there in the cartridge after the delivery of the final dose.

It may be another aspect of the invention that the fluid delivery pen may have a dose drive mechanism which may ensure easier and accurate dose delivery by minimizing the forces a user must apply to inject a dose by a reduced friction by an improved shape and appropriate length of the thumb pad and reduced contact surface with the mating of dose setting component.

It may be another aspect of the invention that fluid delivery pen may be more slender, reduced diameter of the various key components such as housing, dose setting drums and dose knob, and also reduced overall weight and length.

It may be another aspect of the invention that the fluid delivery pen lid or pen cap would have an internal orientation which would impart not only better aesthetic look but also firmer or tighter snap on the cartridge cover or fluid cartridge holder for better protection of the internal components.

It may be another aspect of the invention to the fluid delivery pen would have an audible click as the dose dial returns to "0" indexing.

The exterior of the fluid delivery pen of the present invention may comprise the pen cap and the outer body. The pen cap may encapsulate the drug vial or cartridge. The outer body may encapsulate the dose setting/indexing and dose driving mechanisms. The impact resistance of these parts may be important for protection of the mechanism and fluid contents.

The selection of the required dose indexing may be input by the user through rotation of the dose dial tube knob. Tactile feedback may be given via the dial-up and dial-down ratchets, formed in the ratchet cap and clutch tube respectively. Each ratchet may act against an array of teeth, where each tooth may represent a single dosage unit. During indexing or dose setting the dose dial tube can freely rotate in relation to the fixed clutch tube, aided by a sprung loaded dog clutch mechanism. The maximum dose setting may be determined by channels which run longitudinally within the clutch tube.

To deliver the selected dose a force may be applied by the user on to the thumb Pad. This force may be translated, through the ratchet cap to the clutch tube, locking the clutch tube to the dose dial tube. Therefore as the dose dial tube rotates so too the clutch tube may rotate, until the dose dial tube may come to rest at the outer body zero index stop.

During dose delivery the rotational action of the clutch tube may be related to the driveshaft Keyway, via diametrically opposing lugs. The driveshaft keyway may then rotate, overcoming a one-way ratchet on the inner body. Rotation may be translated to the driveshaft, via a square/rectangular shaped bore on the driveshaft Keyway, which may fit over a similarly square/rectangular shaped head on the driveshaft. Two diametrically opposing lugs on the hollow piston rod run along channels on the inner body which may prevent rotation of the hollow piston rod during dosing. The hollow piston rod lugs may contact the end of the inner body channels, locking the pen mechanism from further delivery. This may serve as indicator to the user that the final dose has been delivered.

The cartridge or vial may be fitted within the cartridge cover. It may be aligned axially by a series of ribs, which may run longitudinally inside the cartridge cover. The head and neck of the cartridge may sit within the head and neck regions of the cartridge cover. The cartridge cover may be fixed within the pen assembly by an external circular rib, which may mate with a circular channel on the inside of the outer body. Axial alignment may be aided by a series of ribs distributed about the inside surface of the outer body. Two snap pips may also be placed diametrically opposite, for linear clipping and rotational orientation of the fitted pen Cap.

Terminology used in this present invention may be as follows. Proximal end of a component or component in an assembled pen or the assembled pen is the end that corresponds to the dose setting end. Distal end of a component or component in an assembled pen or the assembled pen is the end that corresponds to the delivery end.

Fluid as used in this present invention may be construed any pharmaceutically active ingredient including insulin, insulin analogues and the like.

The fluid delivery pen device in accordance with the present invention may comprise a cartridge cover for a fluid containing cartridge, two concentrically arranged housing bodies—outer body and inner body and two concentrically arranged dose-drums-dose dial tube and clutch tube. The cartridge cover may carry a fluid containing cartridge. The cartridge may on its distal end carry a needle. The cartridge may on its proximal end carry a plunger. The proximal end of the cartridge cover may have a retention rib which may act as a snap with the outer body retention channel for retaining the cartridge cover into the outer body. The orientation notch provided distal to the proximally located retention rib may align with the inner body orientation tooth and pen assembly. The above mating/attachments of the components inner body, outer body and cartridge cover may ensure secure and proper alignment.

The proximal half of the fluid delivery pen comprises the housing comprising inner body and outer body which encloses the dose setting/dose indexing and drive mechanisms. Two concentrically arranged clutch tube and dose dial tube may be placed between the inner body and outer body. Outer body and inner body may be held in place by the mating of inner rib wall located distal to last dose click rib on the inner surface of the outer body with the datum face and snap tooth of the inner body. The inner rib wall located distal to last dose click rib on the inner surface of the outer body serves two functions. Firstly, inner rib wall of the outer body contacts datum face of inner body to fix linear mate of pen assembly. Secondly, inner rib wall opposes the inner body snap teeth of the inner body which are fitted through hole and ultimately mate to retain the inner body. Further, Outer body and inner body may be prevented from rotation relative to each other by the mating of diametrically opposite anti-rotation rib provided along side the inner rib wall on internal surface of the outer body with the diametrically opposite anti-rotation notch positioned on the proximal end distal to the datum face of the inner body.

Alignment ribs located distal to inner rib wall towards the distal end of the outer body on its inner surface may provide concentric location of the cartridge cover and may help in securing and positioning firmly to the outer body. Located on the inner surface of the outer body proximal to the proximal end of the inner rib wall may be the last dose click rib which forms a click sound on mating with the last dose click ratchet placed diagonally opposite to zero stop notch on the distal surface of the dose dial tube. A zero stop rib on the inner surface of the outer body may run longitudinally in the proximal direction originating from the proximal end of inner rib wall and terminating at the nearest circumferential helical rib. A zero stop notch on the distal surface of the dose dial tube may act as a rotational stop for dose dial tube which may establish thread relationship when the pen returns to zero index on delivery of the fluid by its mating with zero stop rib. The outer body may have helical ribs provided on its inner surface circumferentially which may mate with the helical channel provided circumferentially on its outer surface of the dose dial tube while setting the dose or reducing the dose. The outer body may have a circular snap channel provided internally at its distal end which may work as a bump-off feature that may hold the cartridge cover by snapping with retention rib provided on the outer surface of the cartridge cover outer surface towards the proximal end. This may retain the cartridge cover into the outer body.

The fluid delivery pen may comprise a dose setting/indexing mechanism and a driving mechanism. The fluid delivery pen drive mechanism of the present invention has a feature of reduced friction during dose delivery which may enable the user ease of dose delivery. The fluid delivery pen drive mechanism of the present invention has an additional feature of an indication of end of dose of fluid in a cartridge. The fluid delivery pen does not make use of a component which is rotatable one or a separate movable non rotating member having threaded features for end of dose mechanism unlike in the known fluid delivery pen having the external threaded piston rod. When the component may be axially moving one having threaded features may be vulnerable to wear and tear. As a result of wear and tear inaccuracies may be set in the indication of not only on the repeatedly set doses but also on the remaining doses that may need to be delivered. The rotatable components having threaded features may be further disadvantaged by virtue of entailing high cost precision manufacture of components which may increase the cost of the device. Also it would be desirable that the piston rod may be of strong design. The externally threaded piston rod of the prior art being of relatively small diameter, and may therefore be vulnerable to damage or deformation. Vulnerability to damage or deformation of externally threaded piston rod by virtue of being small may further aggravate the chances of malfunctioning of the end of dose mechanism by the threaded mating of such rotatable component with the external threaded piston rod, which may not be a desirable feature. Further a piston rod that has an internal non-locking helical thread can be substantially larger in diameter and will have a structurally efficient hollow cross section making it substantially stronger than an equivalent externally threaded rod.

The drive mechanism may comprise a hollow piston rod with an inner helical thread and a driveshaft with external helical ribs. Since the driving bore of the drive shaft key way may translate rotation from drive shaft keyway to drive shaft during dose delivery the drive shaft keyway may be considered to be part of the drive mechanism. The proximal portion of the drive shaft comprises a driving head, a snap clip head and shoulder bearing. Further the drive shaft keyway which forms part of the driving mechanism comprises on its proximal portion tooth array. The distal portion of the drive shaft keyway comprises a snap clip fingers, driving lugs and rotational bearings.

Drive shaft may be cylindrical in shape and may have helical ribs provided on its outer surface. Hollow piston rod may be cylindrical in shape and may have helical threads provided on its inner surface. Helical ribs may mate with helical threads and this may translate rotational activation of the driveshaft into linear displacement of the hollow piston rod during dose delivery. Pitch of the thread on drive shaft may determine the ratio of rotational motion to linear displacement. There may be located at the proximal end of the drive shaft, a shoulder bearing which may be cylindrical in shape. This shoulder bearing may displace linear back-pressure due to actuation of the cartridge against inner body bearing surface. Located between the shoulder bearing and snap clip head towards the proximal end of the drive shaft may be the driving head. The driving head surface may mate with the complementary driving bore surface of the drive shaft key way. This mating of driving head surface with the complementary driving bore surface of the drive shaft key way may translate rotation from driveshaft keyway driving bore during dose delivery. Located proximal to driving head and at the proximal end of the drive shaft may be snap clip head. Snap clip head may mate with driveshaft keyway clips which may retain driveshaft keyway within the pen assembly. Located at the proximal end on the outer surface of the hollow piston rod may be two diametrically opposite anti-rotation lugs which interact with inner body anti-rotation channel. Anti-rotation lugs may be two rectangular projections whose side surfaces may interact with inner body anti-rotation channel. This interaction between the anti-rotation lugs and inner body anti-rotation channel may restrict the hollow piston rod rotation during dose activation while translating driveshaft rotation to linear hollow piston rod movement. The distal vertical surfaces of the proximal end diametrically opposite anti-rotation lugs of the hollow piston rod may form lock out surface on contacting last dose stop located distal to the datum face towards distal end of the inner body. This contact between the lock out surface and the last dose stop may prevent linear displacement of hollow piston rod indicating the end of the fluid in the cartridge. This may also be known as final dose stop as no further fluid may be deliverable from the fluid delivery pen. Located at the distal end of the cylindrical hollow piston rod may be a circular piston flange which may push against the cartridge plunger during the dose delivery.

The Fluid delivery pen dose setting/indexing mechanism may comprise a dose dial tube, a clutch tube, a ratchet cap and a thumb pad. The dose dial tube and the clutch tube are located concentrically in between the inner body and outer body. The ratchet cap may be located between the clutch tube and the dose dial tube towards the proximal end of the clutch tube and dose dial tube. The thumb pad is located on the proximal end of the ratchet cap. The Fluid delivery pen dose setting/indexing mechanism of the present invention has a feature of reduced friction during dose delivery which may enable the user ease of dose setting and dose delivery. Another additional feature of fluid delivery pen dose setting mechanism is that it may produce a sound of higher audibility for each click corresponding to one unit dose set and also may produce a sound of lower audibility than the former for each click when the set dose is reduced. The dose setting mechanism to produce a sound while setting a dose or reducing a dose in a fluid delivery pen may seek to reduce the friction between the thumb pad and ratchet components, and to reduce the overall friction of the pen assembly during actuation/use. Reduced friction may be achieved by decreasing the diameter of the force contact area, via an axle/spindle, through which the user may apply direct load to the mechanism. Stability between the parts may be equally important when reducing friction. As such, the parts may be retained using specific bearing surfaces. This may be either as a continuous surface or a series of ribs at each end of the rotating spindle. These bearing features may prevent wobble between the parts and also may provide a minimal contact surface for rotational friction.

The clutch tube has two diametrically opposite one way ratchets at its proximal end which act against one way ratchet teeth of the ratchet cap to provide a click sound during downwards indexing of the doses. The clutch tube has two diametrically opposite clutch springs at its distal end which act against the distal end circumferential internal rib of the dose dial tube to disengage dog teeth located distal to dose dial knob undercut of the dose dial tube during index setting/dose setting. The four longitudinal channels which run circumferentially on the inner surface of the clutch tube partially from distal end to proximal end whose distal ends perform the function of four hard-stops as maximum index stop. The positioning of the four longitudinal channels of the clutch tube and the four driving lugs on the drive shaft key way are such that the driving lugs may move along the clutch tube channels in linear motion. The four longitudinal channels perform two functions in the functioning of the fluid delivery pen. Firstly it may provide telescopic linear motion to driveshaft keyway lugs during dial up/down indexing of doses. Secondly it may translate rotational actuation to driveshaft keyway lugs during dosing of the fluid. Distal to clutch tube drive shoulder on its outer surface there may be provided four dog teeth at 90° to each other. During fluid dosing the dog teeth of the clutch tube may mesh with dose dial tube dog teeth to engage the dosing mechanism. Distal to one way ratchet teeth and proximal to the dog teeth of the clutch tube there may be located a circular drive shoulder. The drive shoulder may carry input force from the ratchet cap drive shoulder during dose activation to engage the clutch mechanism.

The functional description of dose dial tube may be described as follows. Dose dial tube may be cylindrical in shape whose proximal portion which may be known as dose dial knob has a higher diameter than the distal portion. A zero stop notch may be provided on the outer surface of the dose dial tube at its distal end. This may act as a rotational stop against outer body zero stop on the inner surface of the outer body running longitudinally in the proximal direction originating from the distal end of inner rib wall and terminating at the nearest circumferential helical rib. Dose dial grips which may be circumferential ribs may be provided on the outer surface of the dose dial knob of the dose dial tube running from proximal end to distal end of the dose dial knob. Dose dial grips may facilitate easier control of dose dial knob during dose indexing. Dose dial knob may be the proximal portion of the dose dial tube which may have a higher diameter than the lower diameter distal portion. Provided on the outer surface of the dose dial tube may be helical channel which may interact with helical rib of the outer body to form a mating thread relationship. Last dose click ratchet placed diagonally opposite to zero stop notch mates with last dose click rib on the inner surface of the outer body when pen returns to zero index. Dose index/Indices may be provided circumferentially on the outer surface of the dose dial tube which may indicate the number of dialed units of the fluid to be delivered. The dose indices may be range between 0 to 60 units or more in steps of 1 unit. A circular dose dial knob undercut may be located distal to the ratchet teeth and proximal to the dog teeth. The dose dial knob undercut may perform two functions. Firstly, it may retain the ratchet cap within the dose dial tube head. Secondly it may provide linear clearance for dog teeth clutch. The clutch action may include either decoupling during indexing/dose setting or engagement during the delivery of dose. The dog teeth provided distal to the dose dial knob undercut may mesh with clutch tube dog teeth upon thumb pad depression resulting in engagement of dosing mechanism. A circular internal rib may be provided proximal to the distal end of the dose dial tube on its inner surface which may act against clutch springs to disengage the dog teeth during indexing/dose setting. Ratchet teeth may be provided on the inner surface of the dose dial knob of the dose dial tube which may extend from its proximal to distal end terminating at the proximal end of dose dial knob undercut. The ratchet teeth may act against ratchet cap one way ratchet which may act against dose dial tube ratchet teeth to provide a click sound during upwards indexing/dose setting. Upward indexing/dose setting may mean setting of doses in an increased manner. Each tooth of the ratchet teeth may correspond to a single dose increment shown on the dose dial tube index.

Thumb pad may be a component of the dose setting/injection assembly and may be present at the proximal end of the injection device. The thumb pad may be cylindrical in shape and comprises a cylindrical axle pin, three clip teeth, a running surface, and a dose button. The circumferential surfaces of axle pin may form rotational bearings.

Ratchet cap may be considered to have a distal portion and a proximal portion. Both the proximal and distal portion of the ratchet cap may be integrally molded or may have been joined by other standard attachment means. The ratchet cap would function as one component during the operation of the fluid delivery pen. The distal end of the distal portion of the ratchet cap may be of higher diameter than the proximal end of the distal portion of the ratchet cap. The proximal portion of the ratchet cap may comprise a retention rib, a running surface rotational bearings and axle bore. The three retention ribs may be provided at 120° to each other on the proximal end of proximal portion of the ratchet cap. The distal inner surface of the proximal portion of the ratchet cap which may extend partially into the distal portion of the ratchet cap may form the running surface. The inner circular proximal and distal surfaces of the proximal portion of the ratchet cap may function as rotational bearings. The circular opening extending from the proximal end of the proximal portion of the ratchet cap upto the running surface of the proximal portion of the ratchet cap forms the axle bore. The distal portion of the ratchet cap may comprise one-way ratchet teeth, one way ratchet, an axle bore, a drive face and an external rib. The distal portion of the ratchet cap may be cylindrical/circular shape whose distal end may have a circular external rib whose distal end face may form the drive face. Proximal to the external rib may have two diametrically opposite one way ratchet. One way ratchet may have been formed out of the diametrically cut portion in the mid portion on the outer surface of the ratchet cap. Proximal to the external rib in the distal portion of the ratchet cap one way ratchet teeth have been provided circumferentially on its inner surface.

The working mechanism between the thumb pad and the ratchet cap during the operation of the fluid delivery pen may be as follows. The thumb pad lateral assembly may be retained with the ratchet cap by the snapping of the thumb pad clip teeth over ratchet cap retention rib. Further thumb pad axle pin may align with the ratchet cap axle bore. Mating of thumb pad rotational bearings with the ratchet cap axle bore may provide lateral stability between the thumb pad axle pin with reduced friction between the thumb pad and ratchet cap. The running surface of the thumb pad may mate with the running surface of the ratchet cap. The user may apply force on the dose button which force may be transferred from the thumb pad running surface through the thumb pad axle pin on to the running surface of the ratchet cap. The user input force may further be translated through the drive face to result in engagement of the dog clutch mechanism comprising clutch tube dog teeth and dose dial tube dog teeth to activate the delivery of dose. Mating of the rotational bearings surfaces of the ratchet cap and rotational bearing surfaces of the thumb pad may provide lateral stability between the thumb pad axle pin and ratchet cap axle bore.

The working mechanism between the ratchet cap, the clutch tube and the dose dial tube of the fluid delivery pen may be as follows. During the upward dose indexing/dose setting the dose dial tube may rotate in a clock wise or anti clock wise direction depending on the helical orientation of the helical channel on the dose dial tube and the helical rib on the inner surface of the outer body. If the orientation of the helical channel on the dose dial tube may be right handed one then during the upward dose indexing/dose setting the dose dial tube may rotate in a clock wise direction. If the orientations of the helical channel on the dose dial tube may be left handed one then during the upward dose indexing/dose setting the dose dial tube may rotate in an anti-clock wise direction. During the upward dose indexing/dose setting one way ratchet of the ratchet cap may act against dose dial tube ratchet teeth resulting in a click sound. During the downward indexing/dose setting the clutch tube one way ratchet may act against the one-way ratchet teeth of the ratchet cap to provide a click sound. Since the size of the one way ratchet of the ratchet cap may be larger than the size of the one way ratchet of the clutch tube upward dose indexing/dose setting produces a click of higher audibility when acted against dose dial tube ratchet teeth than the downward indexing/dose setting click audibility when acted against one-way ratchet teeth of the ratchet cap. Ratchet cap drive face may carry the input force transferred from the thumb pad through ratchet cap running face to the clutch tube drive shoulder. This input force may enable meshing of the clutch tube dog teeth with dose dial tube dog teeth resulting in engagement of the dosing mechanism during fluid administration. Once the fluid may be fully administered during the next upward or downward indexing/dose setting for the subsequent administration of the fluid the dose dial tube internal rib may act against clutch tube springs for disengagement of dog teeth facilitating the completion of required dose setting. The engagement the clutch tube dog teeth with dose dial tube dog teeth by the thumb pad force transfer and the disengagement of clutch tube dog teeth with dose dial tube dog teeth during next upward or downward indexing/dose setting may be the key to the functioning of the fluid delivery pen.

Described below are some of the embodiments of the present invention. The various embodiments may only serve to illustrate the present invention. It should however be understood that they do not in any way restrict the scope of the invention. It may however be possible for a person skilled in the art to make obvious modifications to various components of a delivery device, for example, changes to cartridge holder or to dose drum, plunger, etc. to arrive at a similarly functional design and the instant invention may be deemed to encompass all such modifications.

The specific embodiment of the invention is described in detail with references to the drawing. The delivery devices described in the following embodiments have the overall shape and appearance of a pen, and have been described, in these embodiments, as fluid delivery pen.

DETAILED DESCRIPTION

Figure 1:
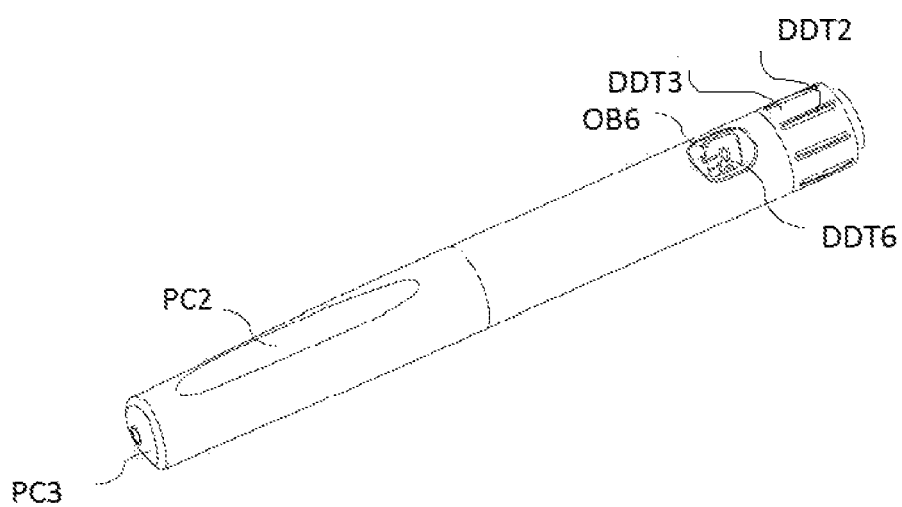
FIG. 1 is a Front ¾ view of fully assembled fluid delivery pen with pen cap in place.
Figure 24:
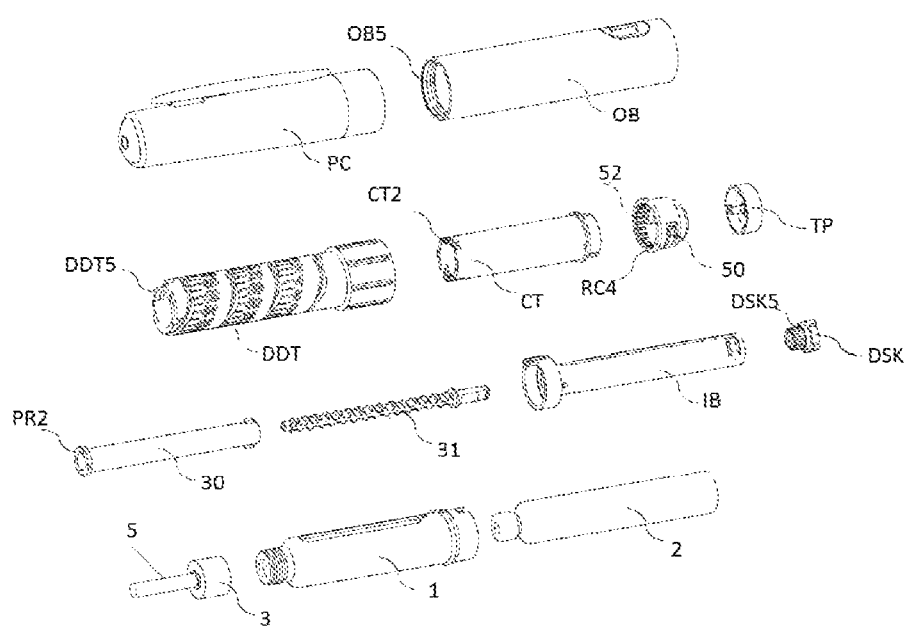
FIG. 24 shows the exploded Front ¾ view of the fluid delivery pen components.
Figure 25:
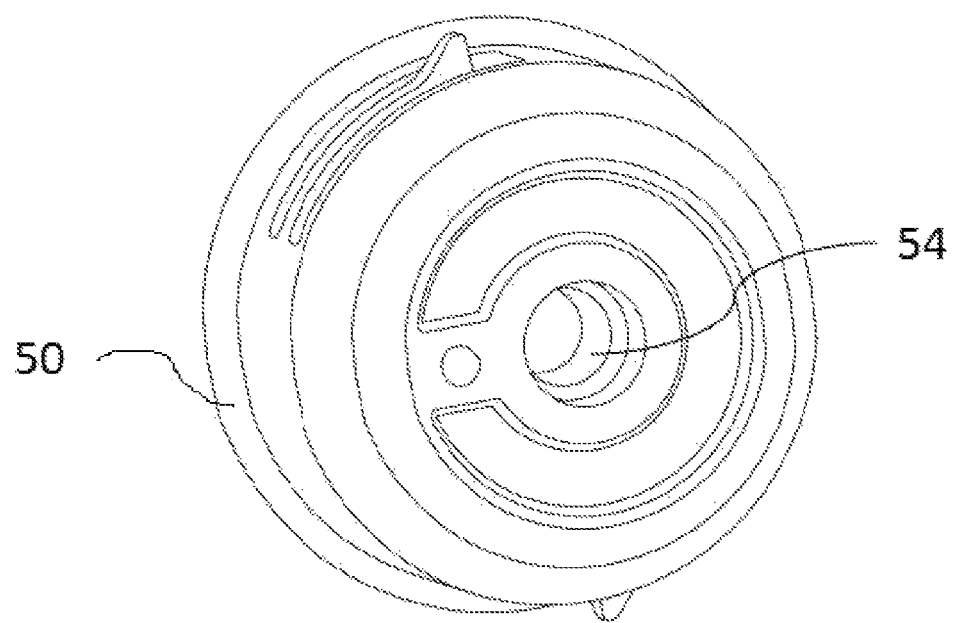
FIG. 25 shows ratchet cap, part with linear bearing surface of the fluid delivery pen.
Figure 26:
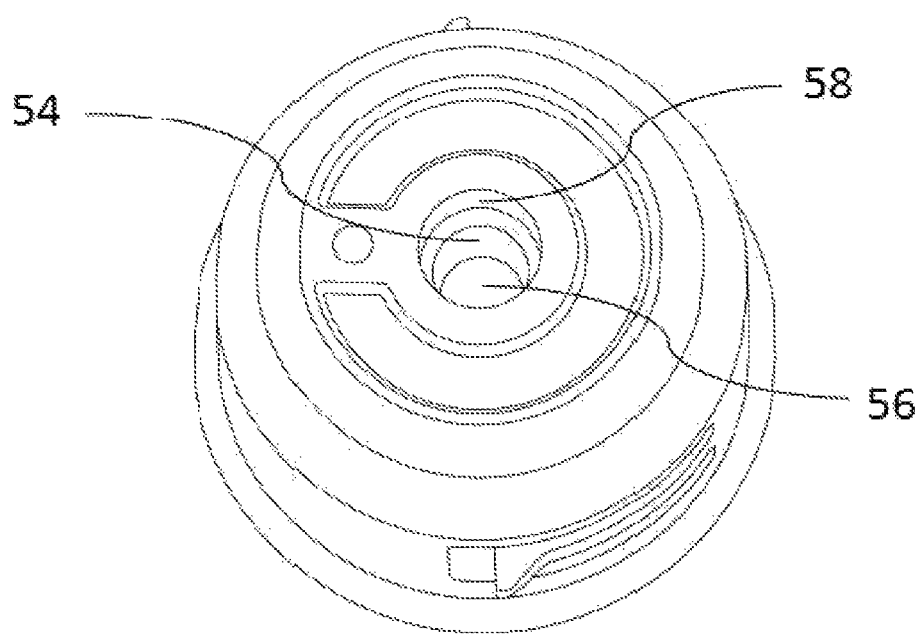
FIG. 26 shows ratchet cap part, with bore feature and rotational bearing surfaces of the fluid delivery pen.
Figure 27:
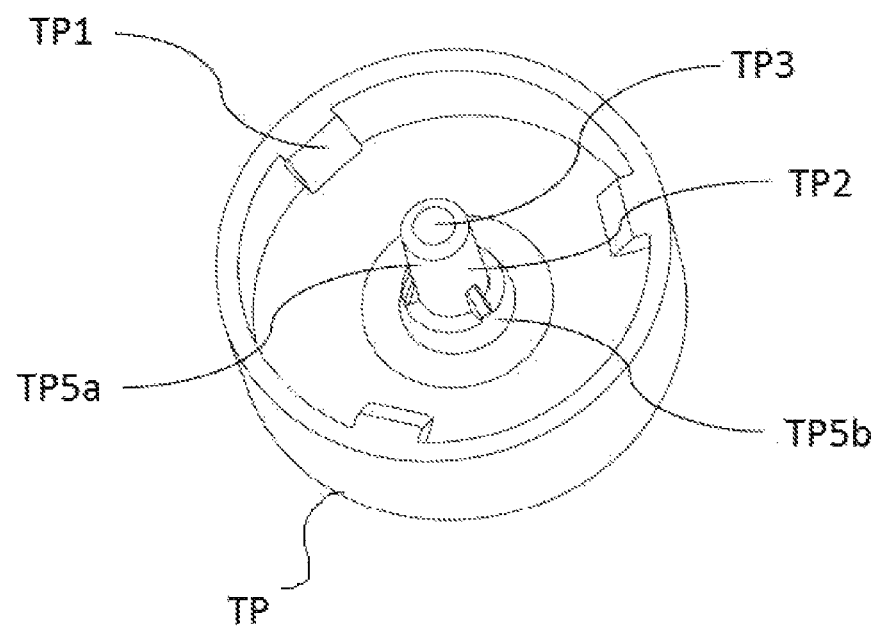
FIG. 27 shows thumb part, with protrusion feature, linear and rotational bearing surfaces of the fluid delivery pen.

FIG. 1 shows the fluid delivery pen in its fully assembled and capped form. This Figure exemplifies that embodiment of the present invention, wherein the delivery device has the overall shape and appearance of a pen. Thus, FIG. 1 exemplifies the pen cap insert (PC3), the pen cap clip (PC2), dose dial window (OB6), dose dial grip (DDT2), dose index (DDT6) and dose dial knob (DDT3). FIG. 24 shows the exploded view of the all the fluid delivery pen components.

Figure 2:
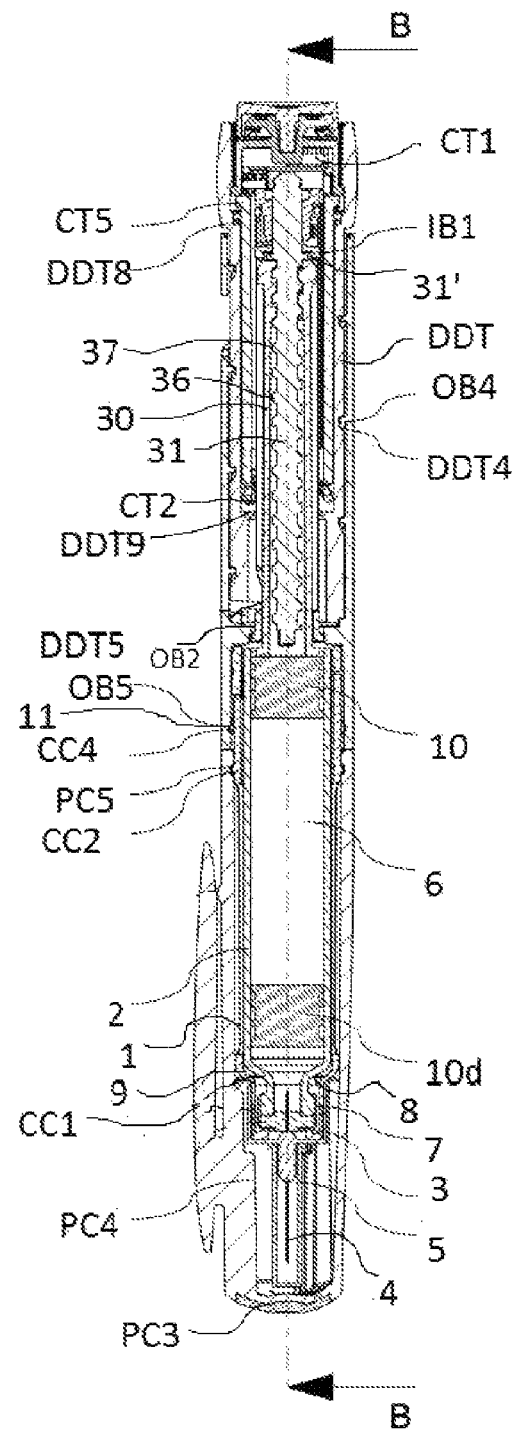
FIG. 2 is sectional view of fluid delivery pen through dose window.
Figure 3:
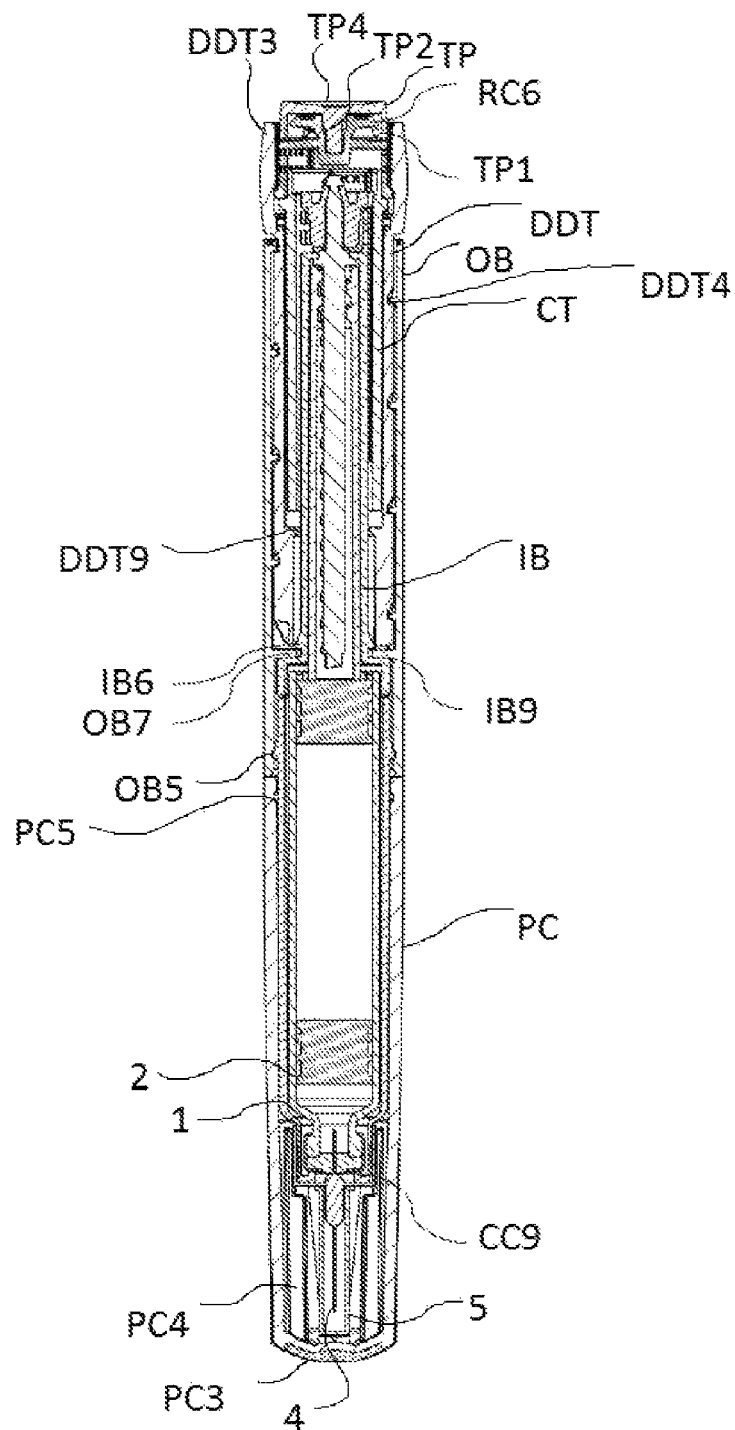
FIG. 3 is a sectional view of fluid delivery pen at 90° with respect to FIG. 2.

With reference to the embodiments shown in FIGS. 2-3, the fluid delivery pen can be described as comprising two regions. The distal half of the pen comprises the cartridge cover (1) for holding the fluid (6) containing cartridge (2). On the distal end of the cartridge cover (1) may be mounted the needle hub (3), that carries the needle (4). The portion of the needle (4) that projects out of the cartridge cover (1) may, in turn, is enclosed by a protective needle cover (5). The proximal end of the needle may communicate with the fluid (6) of the cartridge. The cartridge (2), comprising the fluid (6), may be loaded inside the cartridge cover (1) such that the head (7) and neck (8) of the cartridge may be snugly fixed into the neck region (9) of the cartridge cover (1). The distal end of the cartridge may be sealed, but the proximal portion of the needle may traverse through it in order to communicate with cartridge fluid (6). The proximal end of the cartridge may be enclosed by an airtight, but movable, plunger (10, 10d) (10d) being the plunger after all the available medication has been completely ejected). The outer surface of the cartridge cover (1), on its proximal end, may have helical threads (11).

Figure 16:
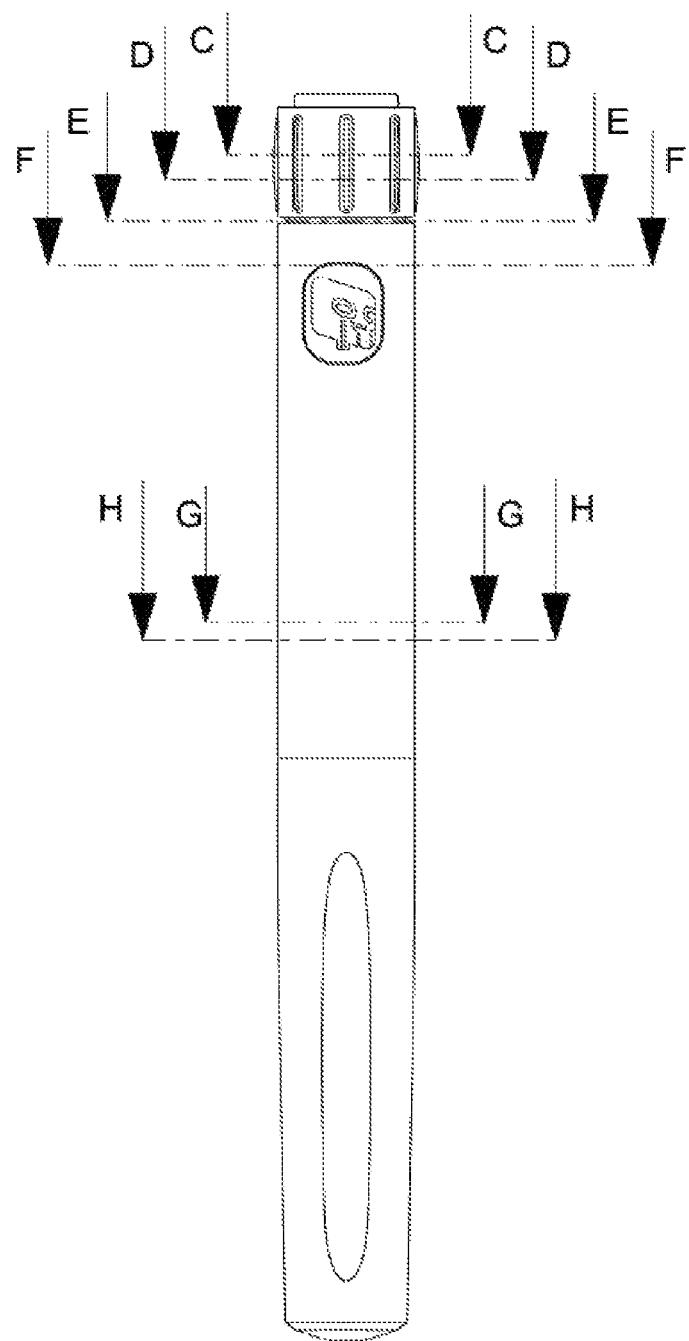
FIG. 16 shows the fluid delivery pen—X section arrows.
Figure 22:
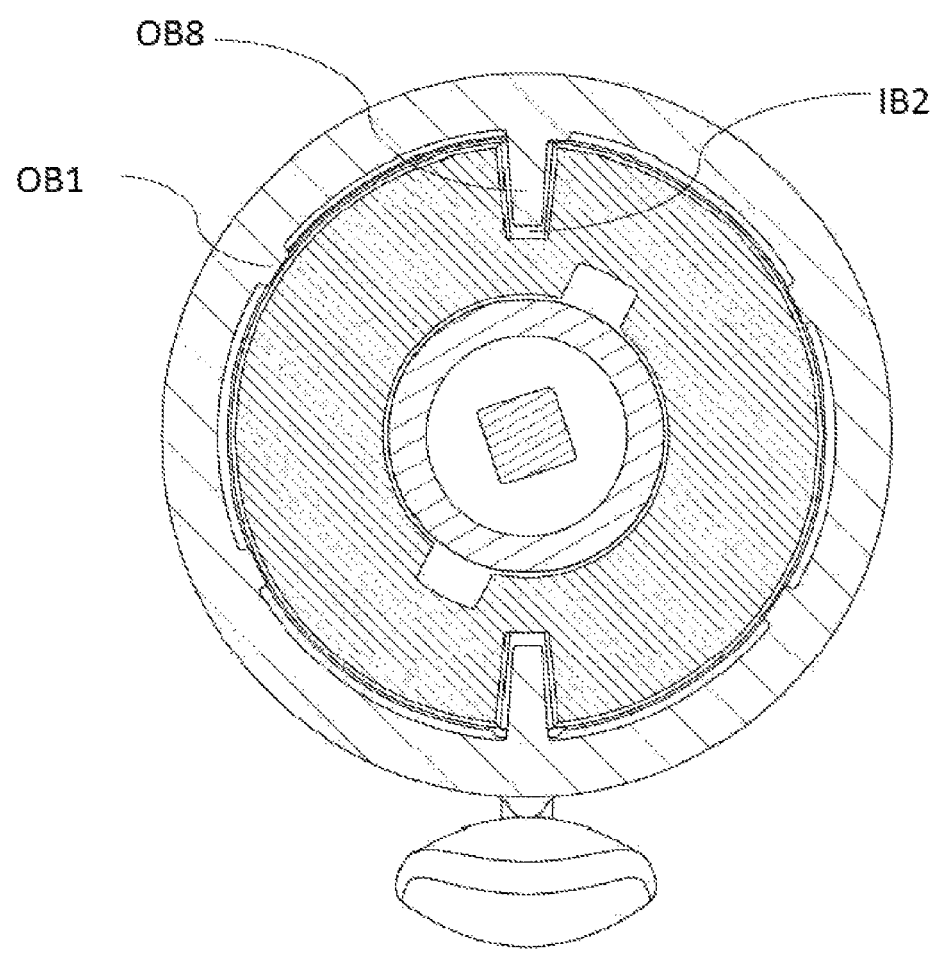
FIG. 22 shows the section H-H of FIG. 16—Inner body anti rotation and alignment ribs feature.

The proximal half of the fluid delivery pen comprises the housing comprising inner body (IB) and outer body (OB) which encloses the dose setting/dose indexing and drive mechanisms. Outer body (OB) and inner body (IB) may be held in place (Refer FIG. 2, FIG. 3, FIG. 9, FIG. 11 and FIG. 13) by the mating of inner rib wall (OB7) located distal to last dose click rib (OB2) on the inner surface of the outer body (OB) with the datum face (IB9) and snap tooth (IB6) located proximal to the datum face (IB9) of the inner body (IB). Inner body (IB) may have diametrically opposite one way ratchet (IB4) provided on the proximal end. Distal to the one way ratchet (IB4) on the proximal end of the inner body (IB) a bearing surface (IB1) may be located. The bearing surface (IB1) may be circular one provided on the inner surface of the inner body (IB). Distal to the bearing surface may be diametrically opposite anti-rotation channel (IB7) running from the proximal end to the distal end of the inner body (IB). It may be noted that the diametrically opposite location of anti-rotation notch (IB2), last dose stop (IB5) and anti-rotation channel (IB7) of the inner body (IB) may be with reference to last dose stop (IB5) location. In one of the embodiments of the invention anti-rotation notch (IB2), last dose stop (IB5) and anti-rotation channel (IB7) and orientation tooth (IB3) may all be located in the same line. The continuing portion of the anti-rotation channel (IB7) towards its distal end may form a bayonet channel (IB8). The outer body (OB) inner rib wall (OB7) and anti-rotation rib (OB8) are located towards its distal end and proximal to circular snap channel (OB5). The inner rib wall (OB7) located distal to last dose click rib (OB2) on the inner surface of the outer body (OB) serves two functions. Firstly, inner rib wall (OB7) of the outer body (OB) contacts datum face (IB9) of inner body (IB) to fix linear mate of pen assembly. Secondly, inner rib wall (OB7) opposes the inner body snap teeth (IB6) of the inner body (IB) located on the outer surface proximal to the datum face (IB9) which are fitted through hole and ultimately mate to retain the inner body (IB). Further, Outer body (OB) and inner body (IB) may be prevented from rotation relative to each other by the mating of diametrically opposite anti-rotation rib (OB8) provided along side the inner rib wall (OB7) on internal surface of the outer body (OB) with the diametrically opposite anti-rotation notch (IB2) positioned on the proximal end distal to the datum face (IB9) of the distal end of the inner body (IB) as shown in FIG. 22 section H-H of FIG. 16. The location of anti-rotation rib (OB8) would be in the same line with reference to last dose stop (IB5) provided in the distal end on the outer surface of the inner body (IB).

Figure 4:
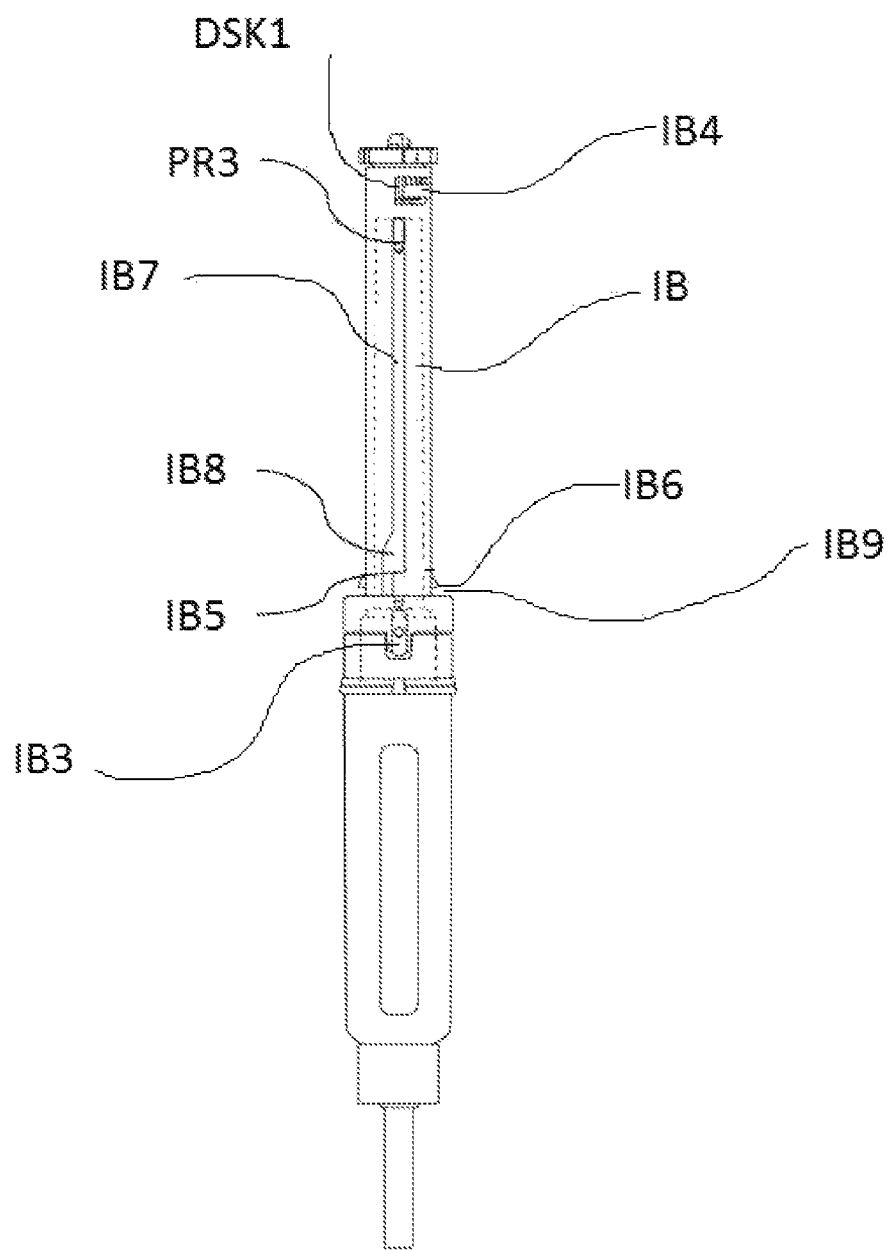
FIG. 4 shows the hollow piston rod of the fluid delivery pen at initial position.
Figure 5:
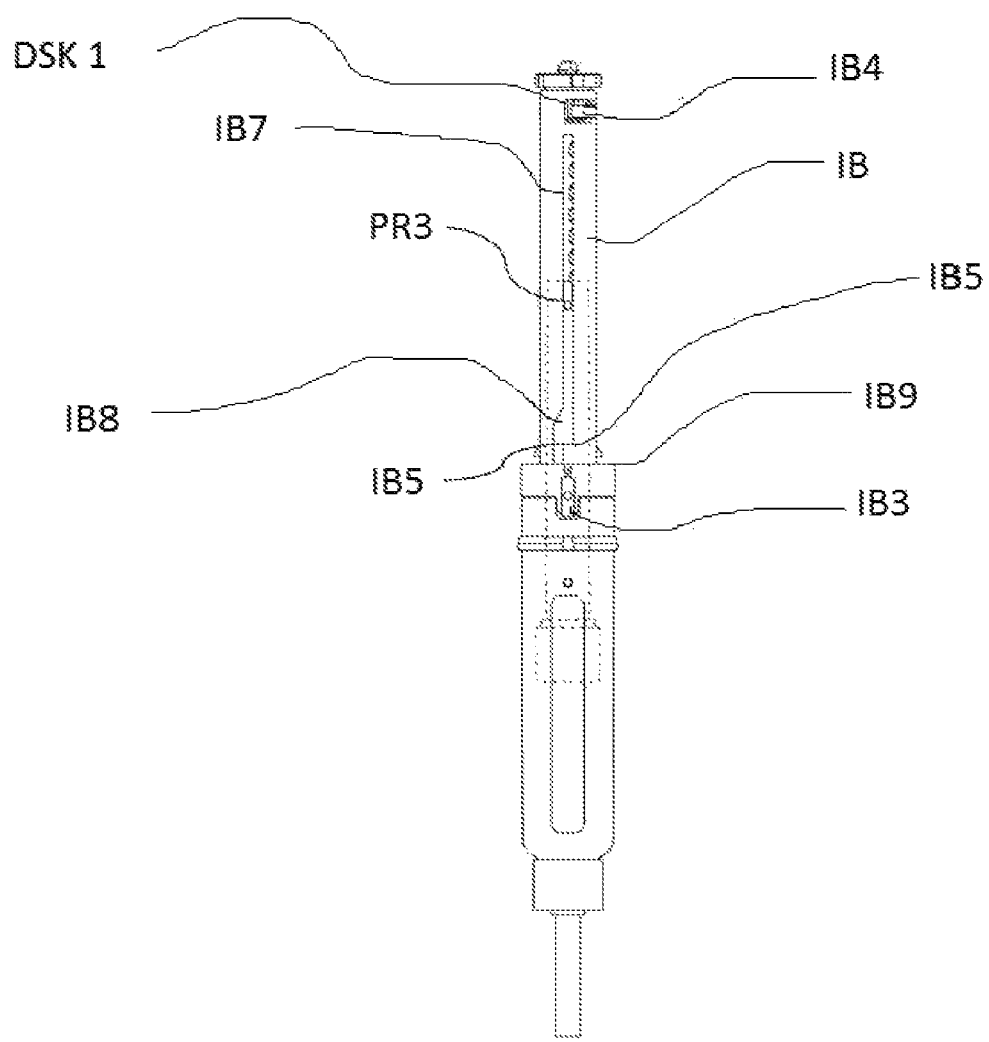
FIG. 5 shows the hollow piston rod of the fluid delivery pen at mid-way position.
Figure 6:
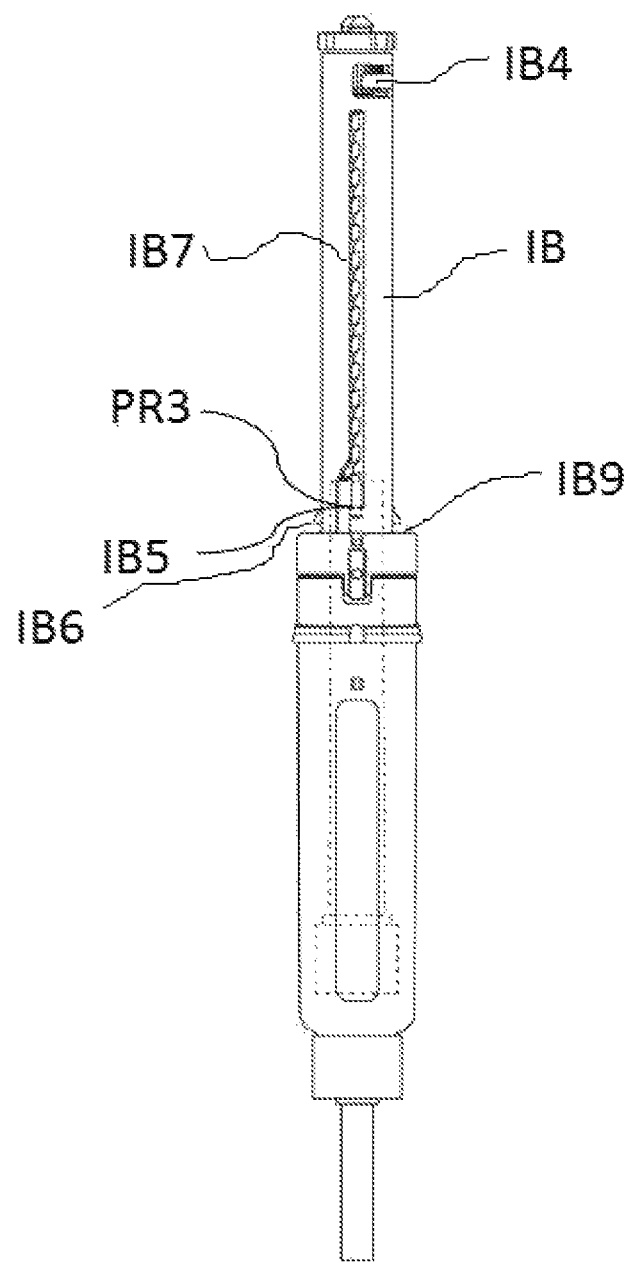
FIG. 6 shows the hollow piston rod of the fluid delivery pen at end of dose position.
Figure 7:
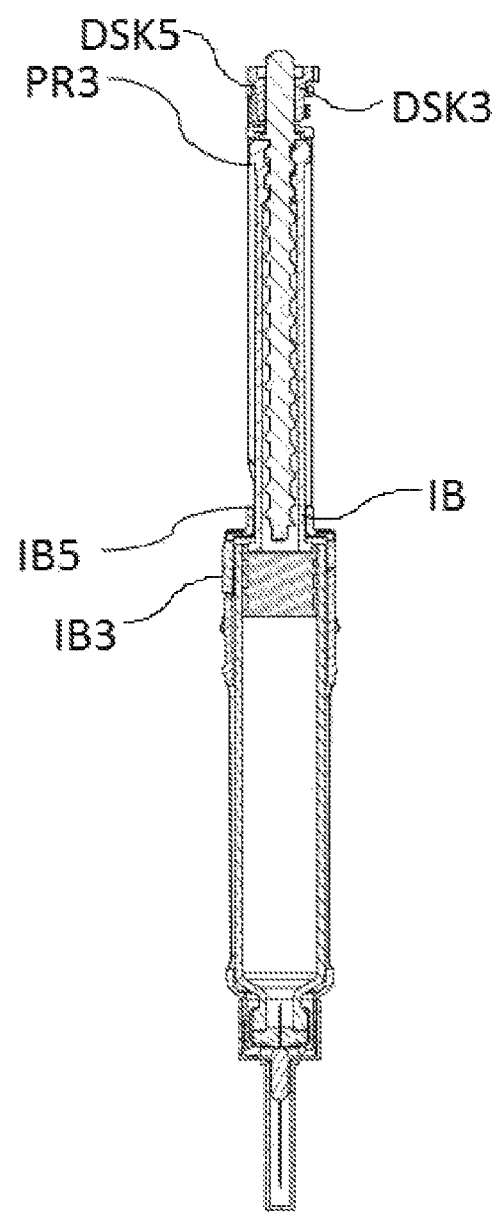
FIG. 7 shows the fluid delivery pen with sectional view of final dose stop in initial use position.
Figure 8:
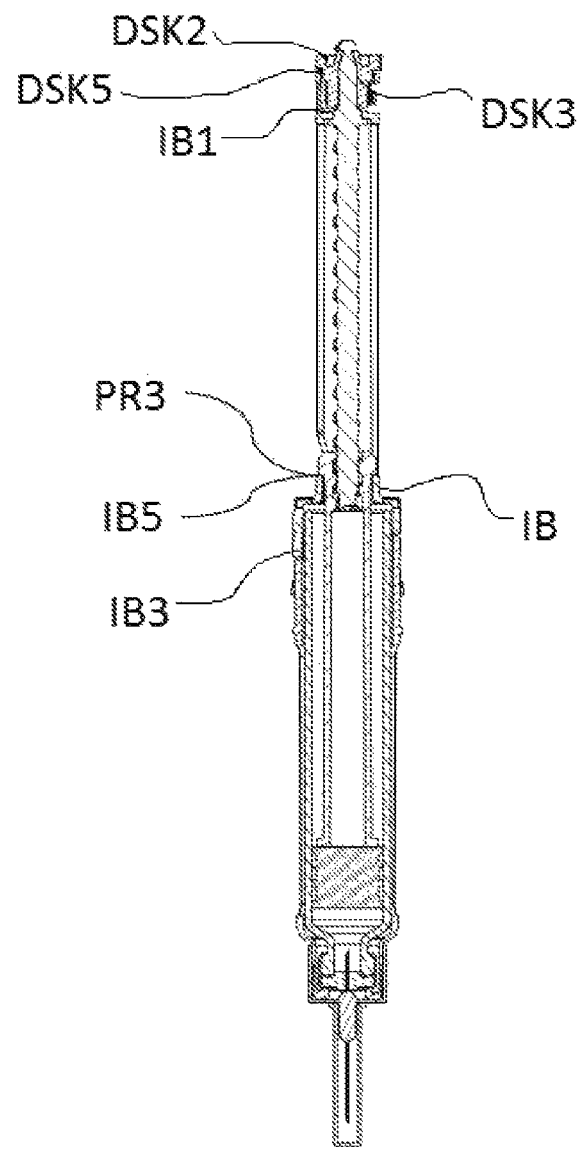
FIG. 8 shows the fluid delivery pen with sectional view of the final dose stop in end of dose position.

Drive shaft (31) may be cylindrical in shape and may have helical ribs (36) provided on its outer surface. The drive shaft (31) proximal portion comprises a driving head (DS2), a snap clip head (DS3) and shoulder bearing (31'). Referring to FIG. 7 and FIG. 8 drive shaft key (DSK) may be located in the proximal portion of the drive shaft (31). The proximal portion of drive shaft keyway (DSK) may be of cylindrical shape of varying diameter the proximal end of which is of higher diameter than the distal one. Located on the outer circumferential surface of the proximal end cylindrical portion of the drive shaft keyway (DSK) may be four driving lugs (DSK4) as shown in FIGS. 9,11,12,13 and 14. A rectangular shaped driving bore (DSK3) may run from proximal end to distal end centrally as shown in FIG. 7 and FIG. 8. Two snap clip fingers (DSK2) may project out from the peripheral proximal end surface of the drive shaft keyway (DSK) as shown in FIG. 11 and FIG. 8. The proximal lower diameter portion of the drive shaft keyway (DSK) may form rotational bearings (DSK5) as shown in FIG. 7 and FIG. 8. Further the drive shaft keyway (DSK) which forms part of the drive mechanism comprises on its distal portion tooth array (DSK1) on circumferential surface. The proximal portion of the drive shaft keyway (DSK) comprises a snap clip fingers (DSK2), driving lugs (DSK4) and rotational bearings (DSK5). Circumferential tooth array (DSK1) may be provided on the distal portion of the cylindrical surface of the drive shaft keyway (DSK1) as shown in figures FIG. 4, FIG. 5, FIG. 6, FIG. 10, FIG. 12 and FIG. 14. Hollow piston rod (30) may be cylindrical in shape and may have helical threads (37) provided on its inner surface. Helical ribs (36) may mate with helical threads (37) and this may translate rotational activation of the driveshaft (31) into linear displacement of the hollow piston rod (30) during dose delivery. Pitch of the thread on drive shaft (31) may determine the ratio of rotational motion to linear displacement. There may be located at the distal end of the proximal portion of the drive shaft (31) a shoulder bearing (31') which may be cylindrical in shape. The mating of proximal shoulder bearing (31') against inner body bearing surface (IB1) may displace linear back-pressure due to actuation of the cartridge (2). Located between the proximal end shoulder bearing (31') and the proximal end snap clip head (DS3) may be the driving head (DS2). The driving head (DS2) may be rectangular or square or any other geometrical shape. The driving head (DS2) surfaces may mate with the complementary driving bore (DSK3) surface of the drive shaft key way (DSK). This mating of driving head (DS2) surface may translate rotation from driveshaft keyway driving bore (DSK3) which extends from proximal to distal end during dose delivery. Located proximal to the driving head (DS2) and at the proximal end of the drive shaft (31) may be snap clip head (DS3). Two snap clip head (DS3) may mate with complementary driveshaft keyway clips (DSK2) which may facilitate retaining drive shaft keyway (DSK) within the pen assembly. Located at the proximal end on the outer surface of the hollow piston rod (30) may be two diametrically opposite anti-rotation lugs (PR1) which interact with inner body (IB7) anti-rotation channel (IB7). It may be noted that the diametrically opposite location of anti-rotation lugs (PR1) and lock out surface (PR3) of the piston rod (30) may be referred with reference to the location of last dose stop (IB5) of the inner body (IB). In one of the embodiments of the invention of locations of anti-rotation lugs (PR1) and lock out surface (PR3) on the piston rod (30) would be in the same line as that of last dose stop (IB5) of the inner body (IB). Anti-rotation lugs (PR1) may be two rectangular projections whose side surfaces may interact with inner body (IB) anti-rotation channel (IB7). This interaction between the anti-rotation lugs (PR1) and inner body (IB7) anti-rotation channel (IB7) may restrict the hollow piston rod (30) rotation during dose activation while translating driveshaft (31) rotation to linear hollow piston rod (30) movement (Refer FIG. 13 and FIG. 14). The distal vertical surfaces of the proximal end diametrically opposite anti-rotation lugs (PR1) of the hollow piston rod (30) may form diametrically opposite lock out surface (PR3) which may contact last dose stop (IB5) located proximal to the datum face (IB9) towards distal end of the inner body (IB) (Refer FIG. 13 and FIG. 14). This contact between the lock out surface (PR3) and the last dose stop (IB5) may prevent linear displacement of hollow piston rod (30) indicating the end of the fluid (6) in the cartridge (2). The FIG. 4, FIG. 5 and FIG. 6 show the hollow piston rod (30) in dotted lines of the fluid delivery pen at initial, mid-way and end of dose position. Position of the plunger (10) is shown in the dotted lines in the initial, middle and end positions. FIG. 7 shows the sectional views of the fluid delivery pen wherein the final dose stop (i.e. mating of last dose stop (IB5) with the lock out surface (PR3)) in initial use position. FIG. 8 shows the sectional views of the fluid delivery pen wherein the final dose stop (i.e. mating of last dose stop (IB5) with the lock out surface (PR3)) in end of dose position. In FIG. 8 snap clip fingers (DSK2) which may mate with driving head (DS2) is shown. No further fluid (6) may be deliverable from the fluid delivery pen after the mating of last dose stop (IB5) with the lock out surface (PR3). Located at the distal end of the cylindrical hollow piston rod (30) may be a circular piston flange (PR2) which may push against the cartridge plunger (10) during the dose delivery.

Figure 9:
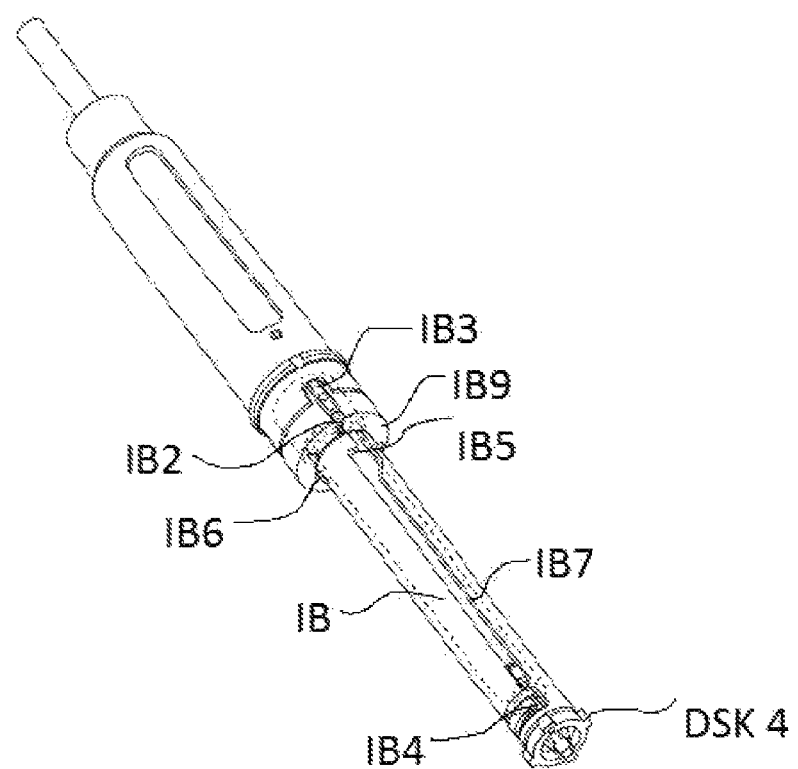
FIG. 9 shows the fluid delivery pen wherein rear ¾ view of hollow piston rod at initial use position.
Figure 10:
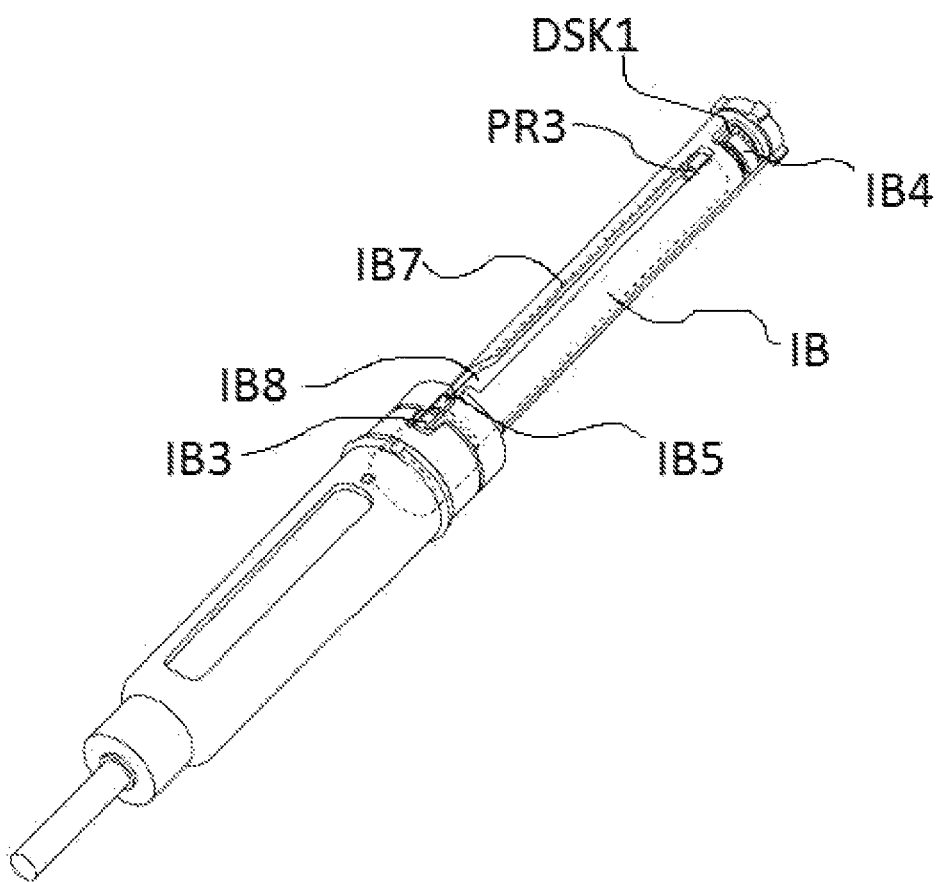
FIG. 10 shows the fluid delivery pen wherein front ¾ view of hollow piston rod at initial use position.
Figure 11:
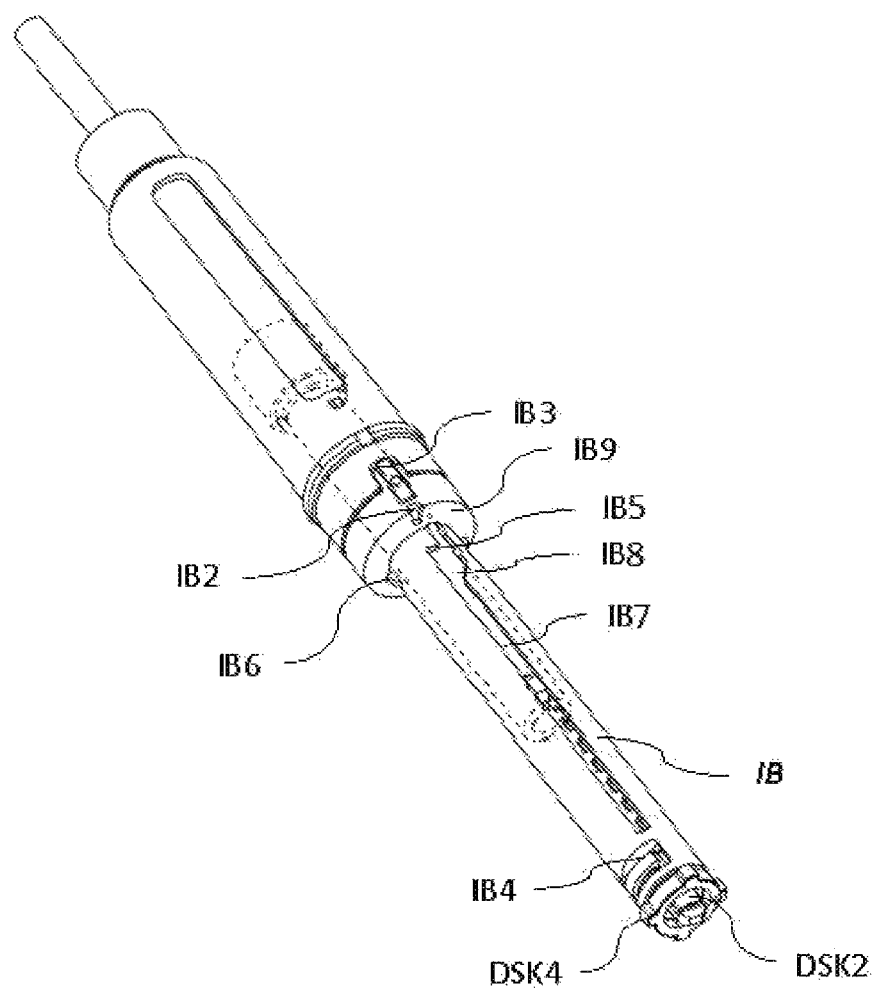
FIG. 11 shows the fluid delivery pen wherein rear ¾ view of hollow piston rod at mid-way position.
Figure 12:
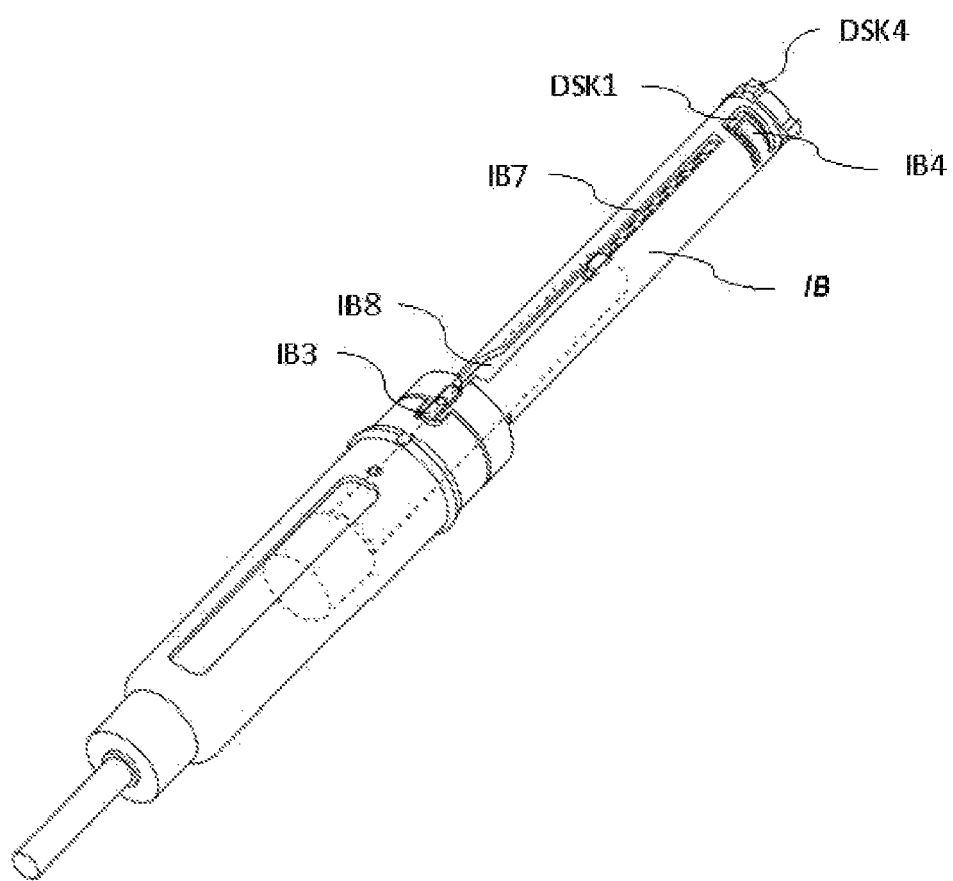
FIG. 12 shows the fluid delivery pen wherein front ¾ view of hollow piston rod at midway position.
Figure 13:
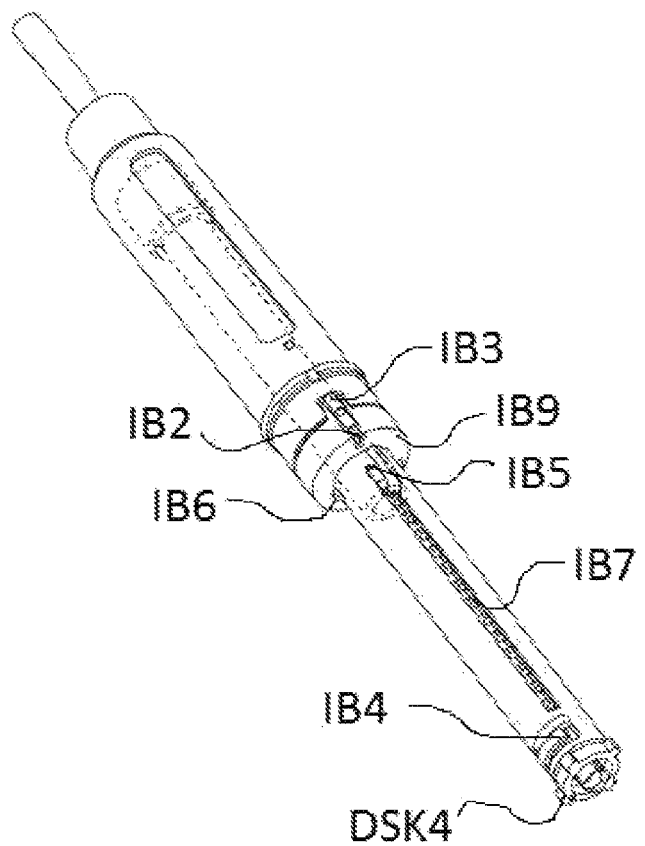
FIG. 13 shows the fluid delivery pen wherein rear ¾ view of hollow piston rod at end of dose position.
Figure 14:
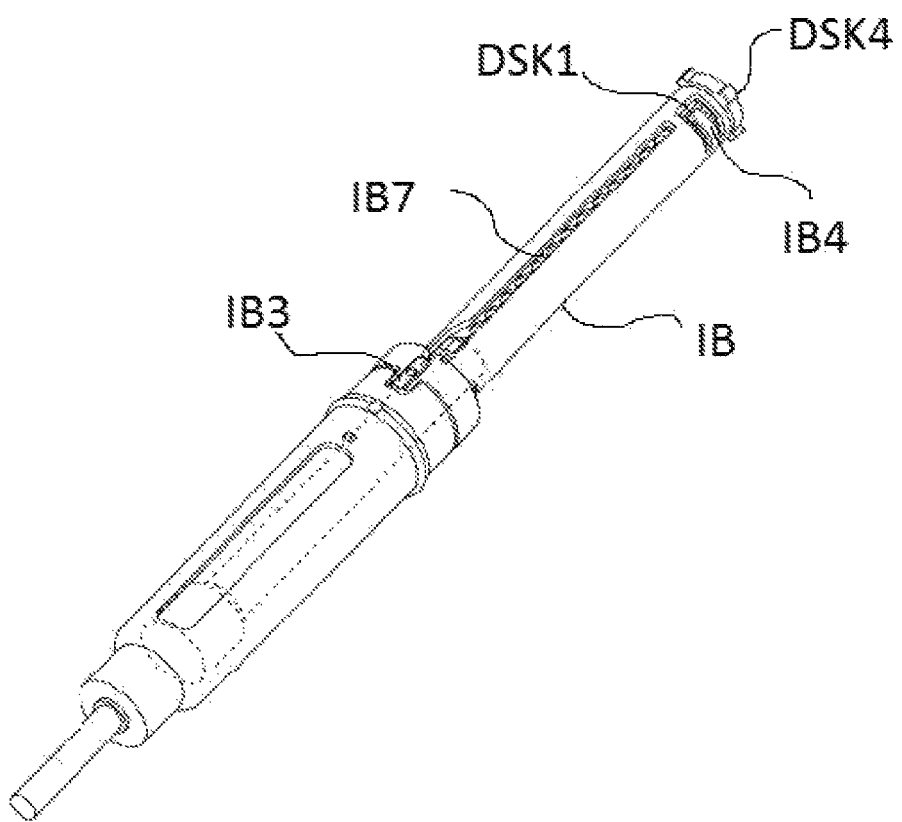
FIG. 14 shows the fluid delivery pen wherein front ¾ view of hollow piston rod at end of dose position.
Figure 15:
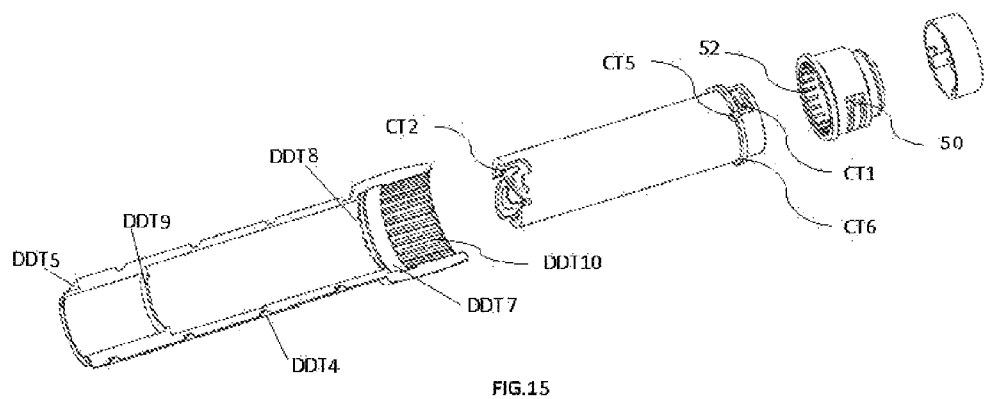
FIG. 15 shows the components of the click mechanism of the fluid delivery pen.

FIG. 9 and FIG. 10 show the rear ¾ and front ¾ views respectively of the fluid delivery pen hollow piston rod (30) at initial use position shown in dotted lines. It may be seen in FIG. 10 that anti-rotation notch (IB2), snap tooth (IB6) and datum face (IB9) of the inner body (IB) are not visible. FIG. 11 and FIG. 12 show the rear ¾ and front ¾ views respectively of the fluid delivery pen hollow piston rod (30) at mid-way position shown in dotted lines. FIG. 13 and FIG. 14 show the rear ¾ and front ¾ views respectively of the fluid delivery pen hollow piston rod (30) at end of dose position shown in dotted lines.

Figure 21:
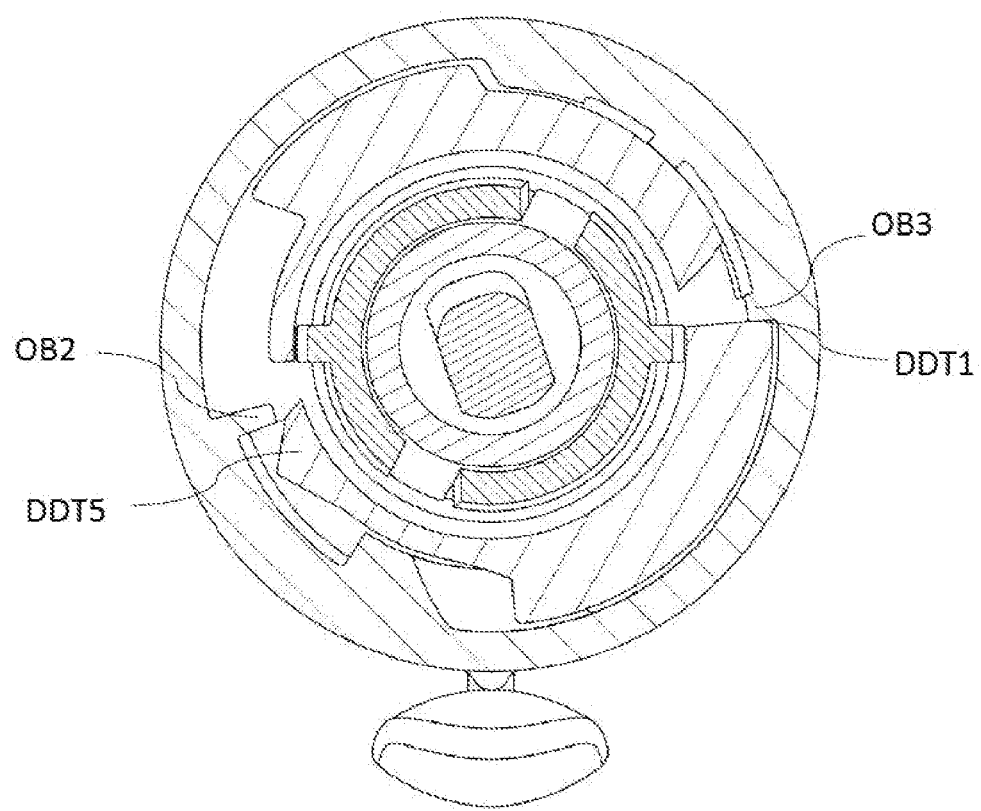
FIG. 21 shows the section G-G of FIG. 16—Last dose click and zero stop features.

Referring to FIG. 2 and FIG. 3 alignment ribs (OB1) located distal to inner rib wall (OB7) on its inner surface at the distal end of the outer body (OB) provides concentric location of the cartridge cover (1) and helps in securing and positioning firmly to the outer body (OB). Located on the inner surface of the outer body (OB) proximal to the proximal end of the inner rib wall (OB7) may be the last dose click rib (OB2) which forms a click sound on mating with the last dose click ratchet (DDT5) placed diagonally opposite to zero stop notch (DDT1) on the distal surface of the dose dial tube (DDT). A zero stop rib (OB3) on the inner surface of the outer body (OB) may run longitudinally in the proximal direction originating from the proximal end of inner rib wall (OB7) and terminating at the nearest circumferential helical rib (OB4). The zero stop rib (OB3) may be of rectangular shape. A zero stop notch (DDT1) on the distal surface of the dose dial tube (DDT) may act as a rotational stop for dose dial tube at zero dose index by its mating with zero stop rib (OB3) as shown in FIG. 21 section G-G of FIG. 16. The outer body (OB) may have helical ribs (OB4) provided on its inner surface circumferentially which may mate with the helical channel (DDT4) provided circumferentially on its outer surface of the dose dial tube (DDT) which may establish thread relationship while setting the dose or reducing the dose. The outer body (OB) may have a circular snap channel (OB5) provided internally at its distal end which may work as a bump-off feature that may hold the cartridge cover (1) by snapping with retention rib (CC4) provided on the outer surface of the cartridge cover (1) outer surface towards the proximal end. This may retain the cartridge cover (1) into the outer body (OB). A dose dial window may be provided on the outer surface of the outer body (OB) towards the proximal end which may enable the viewing of the doses set.

Pen cap (PC) may encapsulate the drug vial or cartridge (2) comprising cartridge neck (8), cartridge head (7), cartridge neck region (9) enclosed in a cartridge cover (1) and the needle assembly comprising needle hub (3), needle (4) and needle cap (5). The pen cap (PC) may be removed to allow fitting of the needle and injection of dose and re-fitted to protect from the contaminants.

Figure 23:
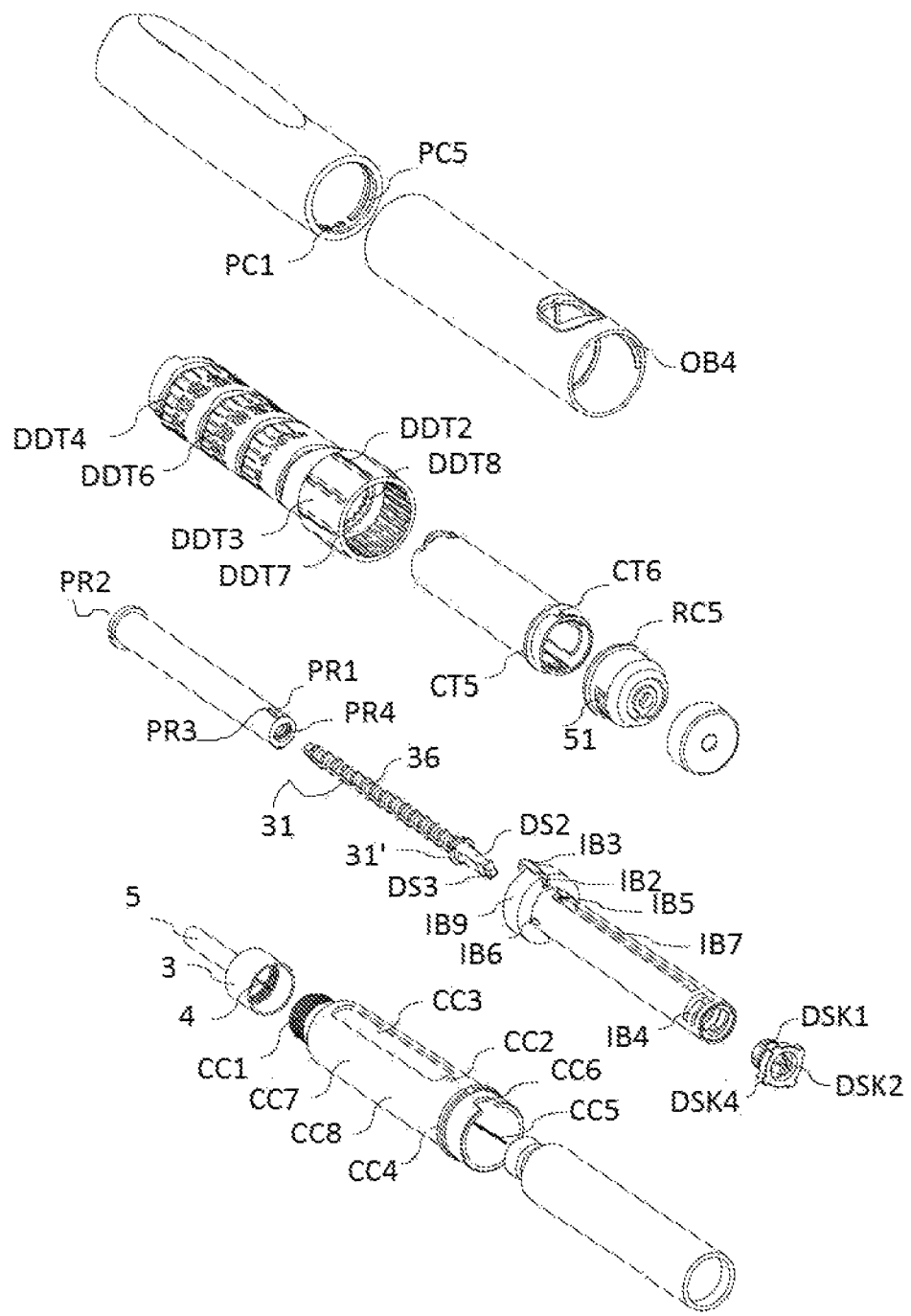
FIG. 23 shows the exploded Rear ¾ view of the fluid delivery pen components.

Referring to FIG. 23 the features of the cartridge cover (1) which may enable its attachment to the pen assemblage may be explained as follows. Located towards its proximal portion on the outer surface of the cartridge cover (1) may be diametrically opposite rotational orientation (CC2) feature, a circular retention rib (CC4) and an orientation notch (CC6). An orientation notch (CC6) may be located on the proximal end outer surface of the cartridge cover (1) which may be in alignment with the viewing window (CC3). The location of orientation notch (CC6) on the cartridge cover (1) would be such that it would be in alignment with the orientation tooth (IB3) of the inner body (IB). The orientation notch (CC6) may be in rectangular in shape formed out of a cut in the distal circumferential surface of the cartridge cover (1). Located on the outer surface of the cartridge cover (1) distal to the distal end of the orientation notch (CC6) and proximal to the rotational orientation feature (CC2) may be a circular retention rib (CC4). Located distal to the circular retention rib (CC4) and proximal to the viewing window (CC3) on the outer surface may be diametrically opposite rotational orientation (CC2) feature. One of the rotational orientation features (CC2) may be in alignment with the orientation notch (CC6) and the viewing window (CC3). The rotational orientation feature (CC2) may be a projection on the outer surface of the cartridge cover (1) and which projection is in the shape comprising a horizontal rectangular surface in the centre and two inclined rectangular surfaces attached to the horizontal rectangular surfaces at an angle.

FIG. 1, FIG. 2, FIG. 3 and FIG. 23 show the various features of the pen cap (PC) and its mating with the cartridge cover (1) offering firm gripping. The pen cap (PC) distal portion comprises three alignment rib (PC4) on its inner surface and a triangular shaped pen cap insert (PC3) on its distal end. Three alignment ribs (PC4) have been provided on the inner surface of the pen cap (PC) extending partially from the distal end to proximal end at 120° which may help in axial alignment of pen cap (PC) on to the cartridge cover (1) or attached needle hub (3) and cover. Location of one of the alignment ribs (PC4) may be in the same line with reference to last dose stop (IB5) on the distal end on the outer surface of the inner body (IB). The other two alignment ribs (PC4) are at 120° with this as the reference. The proximal portion of the pen cap (PC) comprises an orientation feature (PC1) and a circular snap channel (PC5) on its inner surface. The location of orientation feature (PC1) on the inner surface of the pen cap (PC) would be in the same line with reference to last dose stop (IB5) on the distal end outer surface of the inner body (IB). The firm gripping of the pen cap (PC) to cartridge cover (1) may occur when the orientation feature (PC1) located on the inner surface at its proximal end may align with the rotational orientation (CC2) of the cartridge cover (1) by placing the pen cap (PC) over the cartridge cover (1). Pen cap clip (PC2) may run distal end to proximal end which facilitates tucking the fluid delivery pen firmly inside the pocket. Provision of pen cap insert (PC3) on the distal end of the pen cap (PC3) may enhance the aesthetic look of the pen. A circular snap channel (PC5) which may be in circular alignment with the orientation feature (PC1) at the proximal end of the pen cap (PC) may function as a bump-off feature that snaps in with the cartridge cover (1) facilitating firm gripping. There may be provided at the distal end of inner body (IB) an orientation tooth (IB3) which may mate with the proximal end orientation notch (CC6) of the cartridge cover (1). This mating may ensure alignment of cartridge cover (1) with pen assembly. Cartridge cover (1) distal end may have threads which may be attached to needle assembly. Cartridge cover (1) may have two diametrically opposite viewing window (CC3) on its outer surface which may provide direct visual access to assess remaining fluid (6) in the cartridge visibility.

The features of the cartridge (2) and its mating with the cartridge cover (1) may be explained as follows with reference to FIG. 2, FIG. 3 and FIG. 23. Cartridge (2) may be a standard one comprising a cartridge body which may encapsulate 3 ml or 1.5 ml or any other quantity varying between 0.3 ml to 3 ml. The cartridge body may contact cartridge cover (1) four alignment ribs (CC5) (not shown in FIG. 23) provided on the inner surface of the cartridge cover (1). The four alignment ribs (CC5) may provide concentric axial location for glass cartridge (2). The metal clasp may retain septum and may apply pressure to septum for sealing against cartridge body at the distal end. The head assembly surface of the cartridge (2) may be in contact with cartridge cover retention rib (CC9) (not shown in FIG. 23). This may secure cartridge (2) within the cartridge cover (1). The septum of the cartridge may allow needle piercing to access fluid (6) for delivery. It may also seal the fluid (6) in the cartridge (2) at the distal end. The rubber plunger located at the proximal end of the cartridge (2) may fit the body sealing the fluid (6) at the proximal end. The cartridge volume index (CC7) (not shown in FIG. 23) may be provided from the distal to the proximal end on the cartridge cover (1). The cartridge body (CC8) of the cartridge cover (1) may protect cartridge or vial (2) from damage due to accidental drop scenarios. The cartridge retention rib (CC9) (not shown in FIG. 23) provided on the distal end of the cartridge cover (1) may contact the cartridge head surface to retain the cartridge.

The Fluid delivery pen dose setting/indexing mechanism may comprise a dose dial tube (DDT), a clutch tube (CT), a ratchet cap (50) and a thumb pad (TP). The dose dial tube (DDT) and the clutch tube (CT) are located concentrically in between the inner body (IB) and outer body (OB). The ratchet cap (50) may be located between the clutch tube (CT) and dose dial tube (DDT) towards the proximal end of the clutch tube (CT) and dose dial tube (DDT). The thumb pad (TP) may be located on the proximal end of the ratchet cap (50).

Referring to FIG. 2, FIG. 3 and FIG. 23 the clutch tube (CT) may have two diametrically opposite one way ratchets (CT1) at its proximal end which act against one-way ratchet teeth (52) of the ratchet cap (50) to provide a click sound during downwards indexing of the doses. The clutch tube (CT) has two diametrically opposite clutch springs (CT2) at its distal end which act against the circumferential internal rib (DDT9) located towards the distal portion of the dose dial tube (DDT) to disengage dog teeth (DDT8) located distal to dose dial knob undercut (DDT7) of the dose dial tube (DDT) during index setting/dose setting. The four longitudinal channels (CT4) which run on the inner surface of the clutch tube (CT) partially from distal end to proximal end whose distal ends perform the function as four hardstops as maximum index stop (CT3). The positioning of the four longitudinal channels (CT4) of the clutch tube (CT) and the four driving lugs (DSK4) on the drive shaft key way (DSK) are such that the driving lugs (DSK4) may move along the clutch tube channels (CT4) in linear motion. The four longitudinal channels (CT4) perform two functions in the functioning of the fluid delivery pen. Firstly it may provide telescopic linear motion to driveshaft keyway lugs (DSK4) during dial up or dial down indexing of doses. Secondly it may translate rotational actuation to driveshaft keyway lugs (DSK4) during dosing of the fluid. Distal to clutch tube (CT) drive shoulder (CT6) on its outer surface there may be provided four dog teeth (CT5) at 90° to each other.

During fluid dosing the dog teeth (CT5) of the clutch tube (CT) may mesh with dose dial tube dog teeth (DDT8) of the dose dial tube (DDT) to engage the dosing mechanism. Distal to one way ratchet teeth (CT1) and proximal to the dog teeth (CT5) of the clutch tube (CT) there may be located a circular drive shoulder (CT6). The drive shoulder (CT6) may carry input force from the ratchet cap (50) drive shoulder (RC4) during dose activation to engage the clutch mechanism.

Figure 17:
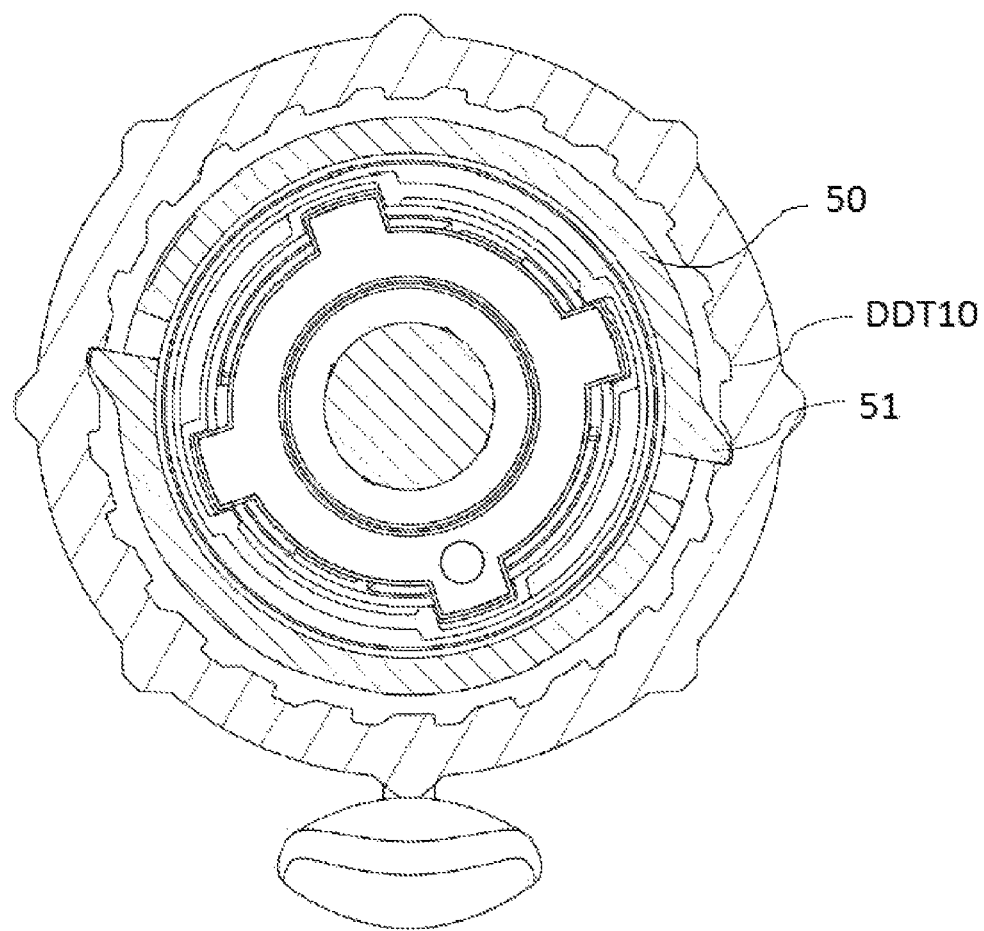
FIG. 17 shows the section C-C of FIG. 16—Dose dial tube and ratchet cap one way ratchet feature.

Referring to FIG. 2, FIG. 3 and FIG. 23 the functional description of dose dial tube (DDT) may be described as follows. The proximal portion of dose dial tube (DDT) comprises dose dial knob (DDT3), dose dial grip (DDT2), dose dial knob undercut (DDT7), dog teeth (DDT8) and ratchet teeth (DDT10). Dose dial tube (DDT) may be cylindrical in shape whose proximal end may be known as dose dial knob (DDT3) which has a higher diameter than distal to dose dial knob (DDT3) distal portion of the dose dial tube (DDT). A zero stop notch (DDT1) may be provided on the outer surface of the dose dial tube (DDT) at its distal end. Zero stop notch (DDT1) may be a small rectangular shaped cut out of the dose dial tube (DDT). This may act as a rotational stop against outer body zero stop (OB3) on the inner surface of the outer body (OB) running longitudinally in the proximal direction originating from the distal end of inner rib wall (OB7) and terminating at the nearest circumferential helical rib (OB4). Dose dial grips (DDT2) are linear ribs provided on the outer surface of the dose dial knob (DDT3) of the dose dial tube (DDT) running from proximal end to distal end of the dose dial knob (DDT3). Dose dial grips (DDT2) may facilitate easier control of dose dial knob (DDT3) during dose indexing. Dose dial knob (DDT3) may be the proximal portion of the dose dial tube (DDT) which may have a higher diameter than the lower diameter distal portion. Provided on the outer surface of the dose dial tube (DDT) may be helical channel (DDT4) which may interact with helical rib (OB4) of the outer body (OB) to form a mating thread relationship. Last dose click ratchet (DDT5) placed diagonally opposite to zero stop notch (DDT1) at the distal end of dose dial tube (DDT) mates with last dose click rib (OB2) on the inner surface of the outer body (OB) forming a click sound when pen returns to zero index as shown in FIG. 21 section G-G of FIG. 16. Dose index/Indices (DDT6) may be provided circumferentially on the outer surface of the dose dial tube (DDT) which may indicate the number of dialled units of the fluid (6) to be delivered. The dose indices may be range between 0 to 60 units or more in steps of 1 unit. A circular dose dial knob undercut (DDT7) may be located distal to the ratchet teeth (DDT10) and proximal to the dog teeth (DDT8) on the inner surface of the dose dial tube (DDT). The dose dial knob undercut (DDT7) may perform two functions. Firstly, it may retain the ratchet cap (50) within the dose dial tube (DDT) head. Secondly it may provide linear clearance for dog teeth (DDT8) clutch. The clutch action may include either decoupling during indexing/dose setting or engagement during the delivery of dose. The dog teeth (DDT8) provided distal to the dose dial knob undercut (DDT7) on its inner surface circumferentially may mesh with clutch tube (CT) dog teeth (CT5) upon thumb pad (TP) depression resulting in engagement of dosing mechanism. A circular internal rib (DDT9) may be provided proximal to the distal end of the dose dial tube (DDT) on its inner surface which may act against clutch springs (CT2) to disengage the dog teeth (DDT8) during indexing/dose setting. Ratchet teeth (DDT10) may be provided on the inner surface of the dose dial knob (DDT3) circumferentially of the dose dial tube (DDT) which may extend from its proximal to distal end terminating at the proximal end of dose dial knob undercut (DDT7). The ratchet teeth (DDT10) of the dose dial tube (DDT) may act against ratchet cap (50) one way ratchet (51) to provide a click sound during upwards indexing/dose setting (shown in FIG. 17 section C-C of FIG. 16). Upward indexing/dose setting may mean setting of doses in an increased manner. Each tooth of the ratchet teeth (DDT10) may correspond to a single dose increment shown on the dose dial tube index.

Thumb pad (TP) may be a component of the dose setting/injection assembly and may be present at the proximal end of the injection device. Referring to FIG. 2, FIG. 3, FIG. 27 and FIG. 28 the thumb pad (TP) features may be described as follows. The thumb pad (TP) may be cylindrical in shape and may have varying diameter cylindrical axle pin (TP2) projecting distally from proximal internal surface at its centre. The proximal end of the axle pin (TP2) may be of a higher diameter than the distal end which may be of a lower diameter within the limitations of the ratchet component dimensions of the fluid delivery pen. There may be three clip teeth (TP1) projecting laterally on the inner peripheral surface of the thumb pad (TP) at 120° to one another. The distal end of the axle pin (TP2) outer surface may form a running surface (TP3). The proximal end of the thumb pad (TP) may form a dose button (TP4). The circumferential surfaces of the higher diameter and lower diameter axle pin may form rotational bearings (TP5; TP5a; TP5b).

Figure 28:
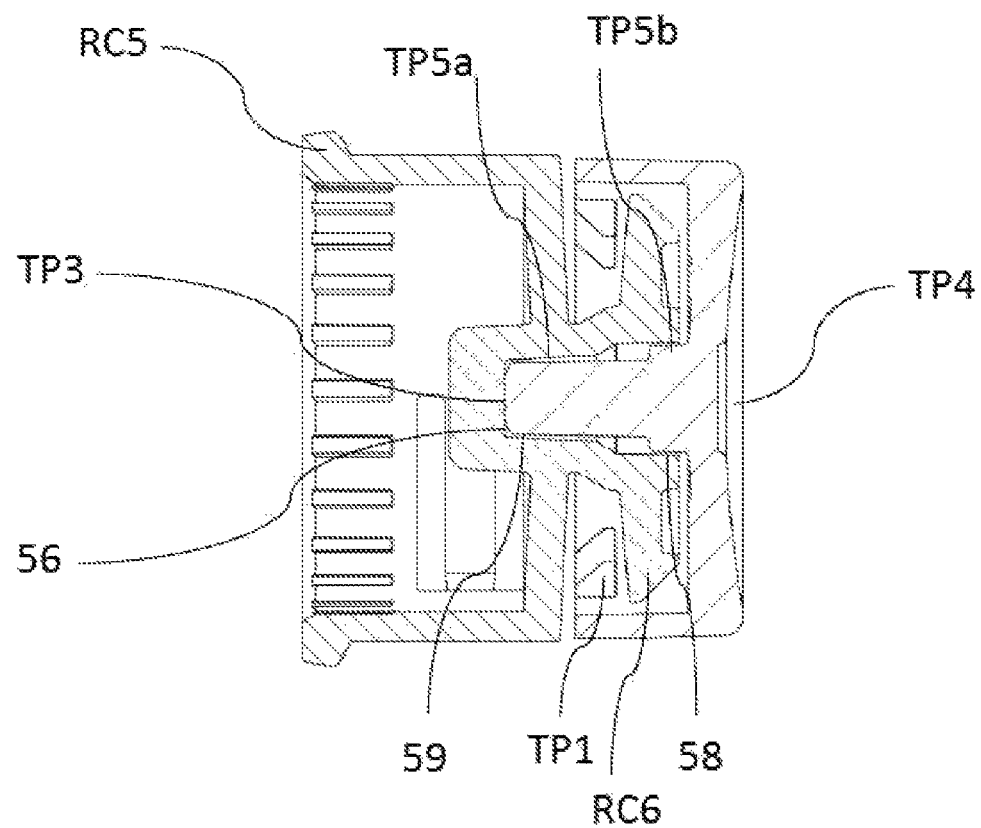
FIG. 28 shows sectional view of assembled parts, showing all critical features and surfaces of the fluid delivery pen.

Ratchet cap (50) may be a component of the dose setting/injection assembly. Ratchet cap (50) is shown in FIG. 15, FIG. 17, FIG. 18, FIG. 25, FIG. 26 and FIG. 28 respectively. Ratchet cap (50) may be considered to have a distal portion and a proximal portion. Both the proximal and distal portion of the ratchet cap (50) may be integrally moulded or may have been joined by other standard attachment means. The ratchet cap (50) would function as one component during the operation of the fluid delivery pen. The distal end of the distal portion of the ratchet cap (50) may be of higher diameter than the proximal end of the distal portion of the ratchet cap (50). The proximal portion of the ratchet cap (50) may comprise a retention rib (RC6), a running surface (56), an axle bore (54), and rotational bearings (58, 59). Referring to FIG. 28, three retention ribs (RC6) (numeral not shown in FIG. 28) may be provided at 120° to each other on the proximal end of proximal portion of the ratchet cap (50). The distal inner surface of the proximal portion of the ratchet cap (50) which may extend partially into the distal portion of the ratchet cap (50) may form the running surface (56). The inner circular proximal and distal surfaces of the proximal portion of the ratchet cap (50) may function as rotational bearings (58, 59).

The distal portion of the ratchet cap (50) may comprise one-way ratchet teeth (52), one way ratchet (51), a drive face (RC4) and an external rib (RC5). The distal portion of the ratchet cap (50) may be cylindrical/circular shape whose distal end may have a circular external rib (RC5) whose distal end face may form the drive face (RC4). External rib (RC5) may facilitate in retaining the ratchet cap (50) within the dose dial tube (DDT) head. Proximal to the external rib (RC5) may have two diametrically opposite one way ratchet (51). One way ratchet (51) may have been formed out of the diametrically cut portion in the mid portion on the outer surface of the ratchet cap (50). Proximal to the external rib (RC5) in the distal portion of the ratchet cap (50) one-way ratchet teeth (52) have been provided circumferentially on its inner surface. The circular opening extending from the proximal end of the proximal portion of the ratchet cap (50) upto the running surface (56) of the proximal portion of the ratchet cap (50) forms the axle bore (54).

Referring to FIG. 17 to 18 and FIGS. 25 to 28 the working mechanism between the thumb pad (TP) and the ratchet cap (50) during the operation of the fluid delivery pen may be as follows. The thumb pad (TP) lateral assembly may be retained with the ratchet cap (50) by the snapping of the thumb pad clip teeth (TP1) over ratchet cap (50) retention rib (RC6). Further thumb pad (TP) axle pin (TP2) may align with the ratchet cap (50) axle bore (RC3). Mating of thumb pad (TP) rotational bearings (TP5) with the ratchet cap (50) axle bore (RC3) may provide lateral stability between the thumb pad (TP) axle pin (TP2) with reduced friction between the thumb pad (TP) and ratchet cap (50). The running surface (TP3) of the thumb pad (TP) may mate with the running surface (56) of the ratchet cap (50). The user may apply force on the dose button (TP4) which force may be transferred from the thumb pad (TP) running surface (TP3) through the thumb pad (TP) axle pin (TP2) on to the running surface (56) of the ratchet cap (50). The user input force may further be translated through the drive face (RC4) to result in engagement of the dog clutch mechanism comprising clutch tube (CT) dog teeth (CT5) and dose dial tube (DDT) dog teeth (DDT8) to activate the delivery of dose. Mating of the rotational bearings (58, 59) surfaces of the ratchet cap (50) and rotational bearing surfaces (TP5, TP5a, TP5b) of the thumb pad may provide lateral stability between the thumb pad (TP) axle pin (TP2) and ratchet cap (50) axle bore (54).

Referring to FIG. 2, FIG. 3 and FIG. 23 the working mechanism between the ratchet cap (50), the clutch tube (CT) and the dose dial tube (DDT) of the fluid delivery pen may be as follows. The helical orientation of the helical channel (DDT4) on the outer surface of the dose dial tube (DDT) is a right handed one then helical rib (OB4) orientation on the inner surface of the outer body (OB) is a left handed one and vice a versa. During the upward dose indexing/dose setting the dose dial tube may rotate in a clock wise or anti clock wise direction depending on the helical orientation of the helical channel (DDT4) on the dose dial tube (DDT) and the helical orientation of helical rib (OB4) on the inner surface of the outer body (OB). If the orientation of the helical channel (DDT4) on the dose dial tube (DDT) may be left handed one then during the upward dose indexing/dose setting the dose dial tube may rotate in a clock wise direction. If the orientation of the helical channel (DDT4) on the dose dial tube (DDT) may be right handed one then during the upward dose indexing/dose setting the dose dial tube may rotate in an anti-clock wise direction. During the upward dose indexing/dose setting one way ratchet (51) of the ratchet cap (50) may act against dose dial tube (DDT) ratchet teeth (DDT10) resulting in a click sound. During the downward indexing/dose setting the clutch tube (CT) one way ratchet (CT1) may act against the one-way ratchet teeth (52) of the ratchet cap (50) to provide a click sound (shown in FIG. 18 section D-D of FIG. 16). Since the size of the one way ratchet (51) of the ratchet cap (50) may be larger than the size of the one way ratchet (CT1) of the clutch tube (CT) upward dose indexing/dose setting produces a click of higher audibility when acted against dose dial tube (DDT) ratchet teeth (DDT10) than the downward indexing/dose setting click audibility when acted against one-way ratchet teeth (50) of the ratchet cap (50). Ratchet cap (50) drive face (RC4) may carry the input force transferred from the thumb pad (TP) through ratchet cap (50) running face (56) to the clutch tube (CT) drive shoulder (CT6) as the drive face (RC4) and the drive shoulder (RC6) surfaces are in direct contact with each other. This input force may enable meshing of the clutch tube (CT) dog teeth (CT6) with dose dial tube (DDT) dog teeth (DDT8) resulting in engagement of the dosing mechanism during fluid administration. Once the fluid (6) may be fully administered, during the next upward or downward indexing/dose setting for the subsequent administration of the fluid (6) the dose dial tube (DDT) internal rib (DDT9) may act against clutch tube springs (CT9) for disengagement of dog teeth (DDT8) facilitating the completion of required dose setting. The engagement the clutch tube (CT) dog teeth (CT6) with dose dial tube (DDT) dog teeth (DDT8) by the thumb pad (TP) force transfer during dose delivery and the disengagement of clutch tube (CT) dog teeth (CT6) with dose dial tube (DDT) dog teeth (DDT8) during upward or downward indexing/dose setting may be the key to the functioning of the fluid delivery pen.

The exterior of the fluid delivery pen may comprise the pen cap (PC) and the outer body (OB). The pen cap (PC) may encapsulate the drug vial or cartridge (2). The outer body (OB) may encapsulate the dose setting/indexing and dose drive mechanisms. The impact resistance of these parts may be important for protection of the mechanism and fluid contents. Both the pen cap (PC) and the outer body (OB) may be handled by the user during use. The pen cap (PC) may be removed to allow fitting of the needle (4) and injection of dose and re-fitted to protect from contaminants. The outer body (OB) may be gripped for dose setting and dose injection. The total product aesthetic may also be heavily determined by the shape of these exterior components, including a colored insert on the end of the pen cap (PC) as well as a pocket clip (PC2).

Figure 18:
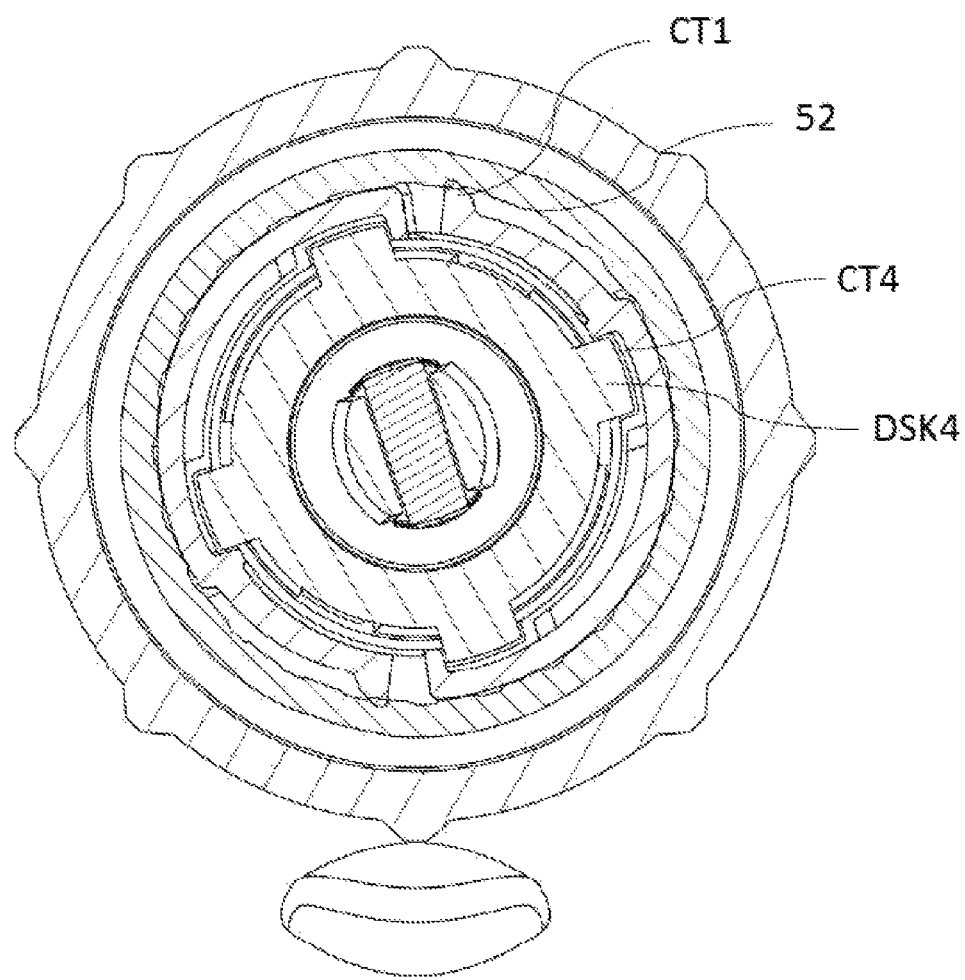
FIG. 18 shows the section D-D of FIG. 16—ratchet cap and clutch tube one way ratchet feature.

The selection of the required dose indexing may be input by the user through rotation of the dose dial tube knob (DDT3). Tactile feedback may be given via the dial-up and dial-down ratchets (51, CT1) formed in the ratchet cap (50) and clutch tube (CT) respectively. Each ratchet may act against an array of teeth (DDT10, 52) where each tooth may represent a single dosage unit. During indexing or dose setting the dose dial tube (DDT) can freely rotate in relation to the fixed clutch tube (CT), aided by a sprung loaded dog clutch mechanism. The maximum dose setting may be determined by channels (CT4) which run longitudinally within the clutch tube (CT). As the dose dial tube (DDT) may be rotationally indexed, the clutch tube (CT) may travel telescopically along the exterior lugs (DSK4) of the driveshaft keyway (DSK) as shown in FIG. 18 section D-D of FIG. 16). At maximum travel the driveshaft keyway lugs (DSK4) may contact the end of the clutch tube channels (CT4) and prevent further indexing or dose setting.

To deliver the selected dose a force may be applied by the user on to the thumb Pad (TP). This force may be translated, through the ratchet cap (50) to the clutch tube (CT), locking the clutch tube (CT) to the dose dial tube (DDT). Therefore as the dose dial tube (DDT) may rotate so too the clutch tube (CT) may rotate, until the dose dial tube (DDT) may come to rest at the outer body (OB) zero index stop (OB3).

Figure 19:
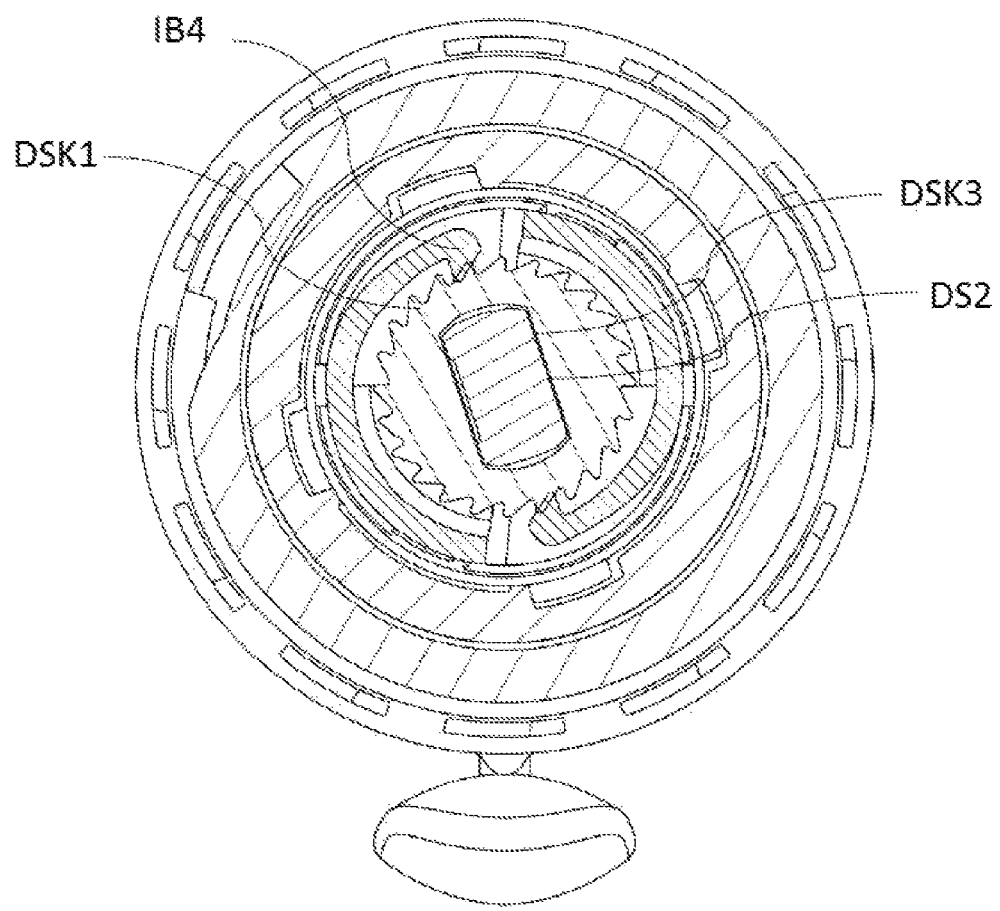
FIG. 19 shows the section E-E of FIG. 16—Inner body and Drive shaft keyway one way ratchet feature.
Figure 20:
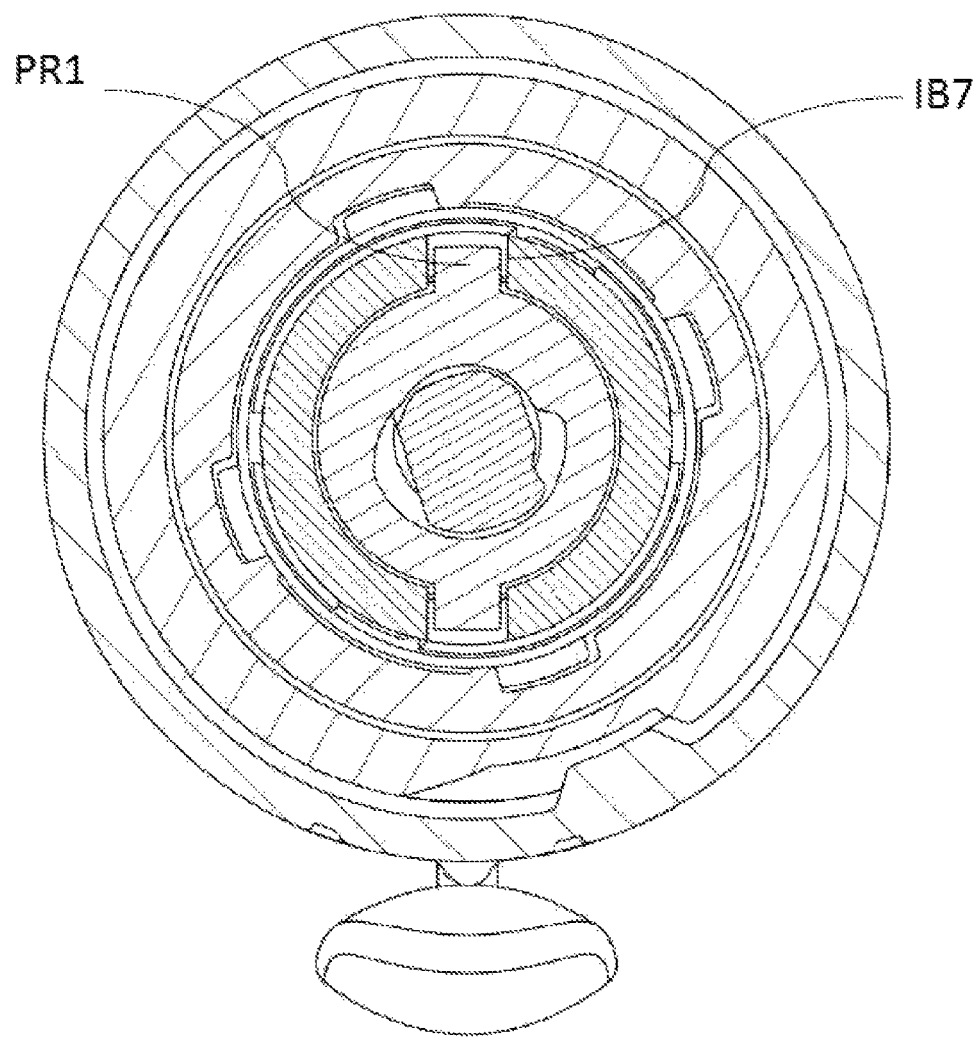
FIG. 20 shows the section F-F of FIG. 16—Piston rod anti-rotation feature.

During dose delivery the rotational action of the clutch tube (CT) may be related to the driveshaft Keyway (DSK), via diametrically opposing lugs (DSK4). The driveshaft keyway (DSK) may then rotate, overcoming a one-way ratchet (IB4) on the inner body (IB). One way ratchet (IB4) may interact with drive shaft key way teeth (DSK1) to prevent counter rotation of mechanism due to compression of fluid within the cartridge vial as shown in FIG. 19 Section E-E of FIG. 16. Rotation may be translated to the driveshaft (31), via a square/rectangular shaped bore (DSK3) on the driveshaft Keyway (DSK), which may fit over a similarly square/rectangular shaped head on the driveshaft (31). Along the length of the driveshaft (31) may be a helical rib (36), which may act within a helical channel (37) on the hollow piston rod (30) to form a driving thread. This thread may translate the rotational actuation of the dosing mechanism into a linear displacement of the hollow piston rod (30). The hollow piston rod (30) head/flange (PR2) then may act against the cartridge plunger (10) to displace fluid from the cartridge (2) or vial. Two diametrically opposing lugs (PR1) on the hollow piston rod (30) run along channels (IB7) on the inner body (IB) which may prevent rotation of the hollow piston rod (30) during dosing as shown in FIG. 20 Section F-F of FIG. 16. The hollow piston rod (30) lugs (PR1) may contact the end of the inner body (IB) anti-rotation channels (IB7), locking the pen mechanism from further delivery. This may serve as indicator to the user that the final dose has been delivered.

The fixing of the cartridge (2) within the cartridge cover (1) and the fixing of the cartridge cover (1) within the pen assembly may be studied with reference to FIG. 2, FIG. 3 and FIG. 23. The cartridge (2) or vial may be fitted within the cartridge cover (1). The cartridge (2) may be aligned axially by a series of rib (CC5), which may run longitudinally inside the cartridge cover (1). The head (7) and neck (8) of the cartridge (2) may sit within the head and neck regions of the cartridge cover (1). A helical thread (CC1) may be located at the distal end of the cartridge cover (1), which may allow for the threaded fitting of a needle (4). The cartridge cover (1) may be fixed within the pen assembly by an external circular rib (CC4), which may mate with a circular channel (OB5) on the inner surface of the outer body (OB) at its distal end. Axial alignment may be aided by a series of ribs (OB1) distributed about the inside surface of the outer body (OB). Running along the length of the cartridge cover (1) body are two diametrically opposite viewing windows (CC3). These may allow the user to visually identify the remaining fluid volume within the cartridge (2) or vial. Two snap pips may also be placed diametrically opposite, for linear clipping and rotational orientation (CC2) of the fitted pen cap (PC).

GLOSSARY

| | | |
|---|---|---|
| OB | Outer Body | Outer Body |
| OB1 | Alignment Ribs | Outer Body |
| OB2 | Last Dose Click Rib | Outer Body |

GLOSSARY

| | | |
|---|---|---|
| OB3 | Zero Stop Rib | Outer Body |
| OB4 | Helical Rib | Outer Body |
| OB5 | Circular Snap Channel | Outer Body |
| OB6 | Dose Dial Window | Outer Body |
| OB7 | Inner Rib Wall | Outer Body |
| OB8 | Anti-Rotation Rib | Outer Body |
| PC | Pen Cap | Pen Cap |
| PC1 | Orientation Feature | Pen Cap |
| PC2 | Pen Cap Clip | Pen Cap |
| PC3 | Pen Cap Insert | Pen Cap |
| PC4 | Alignment Rib | Pen Cap |
| PC5 | Circular Snap Channel | Pen Cap |
| CT | Clutch Tube | Clutch Tube |
| CT1 | One way Ratchet | Clutch Tube |
| CT2 | Clutch Springs | Clutch Tube |
| CT3 | Max Index Stop | Clutch Tube |
| CT4 | Longitudinal channels | Clutch Tube |
| CT5 | Dog Teeth | Clutch Tube |
| CT6 | Drive Shoulder | Clutch Tube |
| DDT | Dose Dial Tube | Dose Dial Tube |
| DDT1 | Zero Stop Notch | Dose Dial Tube |
| DDT2 | Dose Dial Grip | Dose Dial Tube |
| DDT3 | Dose Dial Knob | Dose Dial Tube |
| DDT4 | Helical Channel | Dose Dial Tube |
| DDT5 | Last Dose Click ratchet | Dose Dial Tube |
| DDT6 | Dose Index | Dose Dial Tube |
| DDT7 | Dose Dial Knob Undercut | Dose Dial Tube |
| DDT8 | Dog Teeth | Dose Dial Tube |
| DDT9 | Internal Rib | Dose Dial Tube |
| DDT10 | Ratchet Teeth | Dose Dial Tube |
| TP | Thumb Pad | Thumb Pad |
| TP1 | Clip Teeth | Thumb Pad |
| TP2 | Axle Pin | Thumb Pad |
| TP3 | Running Surface | Thumb Pad |
| TP4 | Dose Button | Thumb Pad |
| TP5 (TP5a, TP5b) | Rotational Bearings | Thumb Pad |
| IB | Inner Body | Inner Body |
| IB1 | Bearing Surface | Inner Body |
| IB2 | Anti-Rotation Notch | Inner Body |
| IB3 | Orientation Tooth | Inner Body |
| IB4 | One-way Ratchet | Inner Body |
| IB5 | Last Dose Stop | Inner Body |
| IB6 | Snap Tooth | Inner Body |
| IB7 | Anti-Rotation Channel | Inner Body |
| IB8 | Bayonet Channel | Inner Body |
| IB9 | Datum Face | Inner Body |
| DSK | Driveshaft Keyway | Driveshaft Keyway |
| DSK1 | Tooth Array | Driveshaft Keyway |
| DSK2 | Snap Clip Fingers | Driveshaft Keyway |
| DSK3 | Driving Bore | Driveshaft Keyway |
| DSK4 | Driving Lugs | Driveshaft Keyway |
| DSK5 | Rotational Bearings | Driveshaft Keyway |
| 1 | Cartridge Cover | Cartridge Cover |
| CC1 | Thread | Cartridge Cover |
| CC2 | Rotational Orientation | Cartridge Cover |
| CC3 | Viewing Window | Cartridge Cover |
| CC4 | Retention Rib | Cartridge Cover |
| CC5 | Alignment Ribs | Cartridge Cover |
| CC6 | Orientation Notch | Cartridge Cover |
| CC7 | Cartridge Volume Index | Cartridge Cover |
| CC8 | Cartridge Body | Cartridge Cover |
| CC9 | Cartridge Retention Rib | Cartridge Cover |
| 11 | Helical threads on outer surface | Cartridge Cover |
| 9 | Neck region | Cartridge Cover |
| 30 | Hollow piston rod | Hollow piston rod |
| PR1 | Anti-Rotation Lugs | Hollow piston rod |
| PR2 | Piston Flange | Hollow piston rod |
| PR3 | Lock-out Surface | Hollow piston rod |
| 37 | Helical Thread | Hollow piston rod |
| 31 | Driveshaft | Drive shaft |
| 36 | Helical Rib | Drive shaft |
| DS2 | Driving Head | Drive shaft |
| DS3 | Snap Clip Head | Drive shaft |
| 31' | Shoulder Bearing | Drive shaft |
| 50 | Ratchet Cap | Ratchet Cap |
| 52 | One way Ratchet Teeth | Ratchet Cap |
| 51 | One way Ratchet | Ratchet Cap |
| 54 | Axle Bore | Ratchet Cap |
| RC4 | Drive Face | Ratchet Cap |
| RC5 | External Rib | Ratchet Cap |
| RC6 | Retention Rib | Ratchet Cap |
| 56 | Running Surface | Ratchet Cap |
| 58, 59 | Rotational Bearings | Ratchet Cap |
| 2 | Cartridge | Cartridge Assembly |
| 6 | Fluid | Cartridge Assembly |
| 10 | Rubber Plunger | Cartridge Assembly |
| 7 | Head | Cartridge Assembly |
| 8 | Neck | Cartridge Assembly |
| 3 | Needle Hub | Needle Assembly |
| 4 | Needle | Needle Assembly |
| 5 | Needle Cover | Needle Assembly |

We claim:

1. A fluid delivery pen comprising:
 (i) a cartridge cover;
 (ii) a pen cap;
 (iii) concentrically arranged an inner body having a proximal end and distal end and an outer body having a proximal end and a distal end, wherein:
  said cartridge cover includes a cartridge containing fluid,
  said inner body includes a drive mechanism for dose delivery,
  said outer body includes a last dose click rib and a zero stop rib provided on an inner surface of the outer body towards the distal end,
  said drive mechanism including a hollow piston rod having a proximal end and a distal end, a drive shaft and a drive shaft keyway,
  said hollow piston rod having a helical thread on its inner surface,
  said drive shaft having a helical rib on its outer surface, the helical thread of the piston rod mating with the helical rib of the drive shaft, forming a thread connection and being axially restrained in the proximal direction relative to the outer body; and
 (iv) a dose setting mechanism that includes, concentrically arranged, a dose dial tube having a proximal end and a distal end, a clutch tube, and a thumb pad, said clutch tube being located inside the dose dial tube, said clutch tube including a one way ratchet on its proximal end, a drive shoulder and dog teeth, said drive shoulder is located distal to the one way ratchet, said dose dial tube and clutch tube being located in between the inner body and the outer body, said dose dial tube having ratchet teeth on its inner surface, a last dose click ratchet, a dose dial knob undercut, a zero stop notch, and dog teeth, said dose dial knob undercut is located proximal to the dog teeth of the dose dial tube, said zero stop notch is provided on the distal end, wherein:
  said dose setting mechanism further includes a ratchet cap having a proximal portion and a distal portion that includes a one way ratchet provided on the distal portion and one way ratchet teeth provided on the inner surface towards the distal portion, the mating of one way ratchet of the ratchet cap with the ratchet teeth of the dose dial tube producing a click of higher audibility during upward dose setting, the mating of the one way ratchet teeth of the ratchet cap with the one way ratchet of clutch tube producing a click of lower audibility during downward dose setting, wherein the size of one way ratchet of the ratchet cap is larger than the size of one way ratchet of the clutch tube, wherein the last dose click ratchet is provided on the distal end of the outer surface of the dose dial tube, said last dose click ratchet of the dose dial tube mates with the last dose click rib of the outer body to provide a click sound when the pen returns to a zero index with the zero stop notch mating with the zero stop rib.

2. The fluid delivery pen of claim 1, wherein dog teeth of the dose dial tube mate with dog teeth of the clutch tube during dose delivery, and the dog teeth of the dose dial tube disengaging from the dog teeth of the clutch tube during dose setting.

3. The fluid delivery pen of claim 1 further comprises a final dose mechanism comprising:
 (i) anti-rotation lugs and a lock out surface on the hollow piston rod; and
 (ii) an anti-rotation channel and a last dose stop on the inner body, wherein the anti-rotation lugs are two diametrically opposite rectangular projections provided at the proximal end on the outer surface of the piston rod, said anti-rotation lugs have side surfaces, distal vertical surfaces of the proximal end diametrically opposite of the anti-rotation lugs of the hollow piston rod are a diametrically opposite lock out surface, an anti-rotation channel runs from the proximal end to the distal end of the inner body, and the side surfaces of the anti-rotation lugs interact with anti-rotation channel of the inner body;
 wherein the mating of the lock out surface of the anti-rotation lugs with the last dose stop of the inner body prevents linear displacement of hollow piston rod indicating the end of the fluid in the cartridge.

4. The fluid delivery pen of claim 1, wherein the proximal portion of the ratchet cap includes a retention rib, rotational bearings, a running surface, and an axle bore.

5. The fluid delivery pen of claim 4, wherein the axle bore formed by a circular opening extending from the proximal end of the proximal portion of the ratchet cap up to the running surface of the proximal portion of the ratchet cap.

6. The fluid delivery pen of claim 4, wherein inner circular proximal and distal surfaces of the proximal portion of the ratchet cap are the rotational bearing.

7. The fluid delivery pen of claim 1, wherein the distal portion further includes a drive face and an external rib.

8. The fluid delivery pen of claim 7 wherein the drive face is the distal end of the distal portion of the ratchet cap.

9. The fluid delivery pen of claim 7, wherein the drive face of the ratchet cap mates with the drive shoulder of the clutch tube, and the external rib of the ratchet cap being located proximal to the drive face.

10. The fluid delivery pen of claim 7, wherein the external rib of the ratchet cap mates with the dose dial knob undercut of the dose dial tube.

11. The fluid delivery pen of claim 1, wherein the dose dial knob undercut is provided on the inner surface of the dose dial tube.

12. The fluid delivery pen of claim 1, wherein the zero stop rib mates with the zero stop notch to provide a rotation stop to the dose dial tube.

13. The fluid delivery pen of claim 1, wherein the thumb pad further includes a cylindrical axle pin and clip teeth, said cylindrical axle pin having a proximal end and a distal end.

14. The fluid delivery pen of claim 13, wherein the distal end of the axle pin form a rotational bearings running surface.

15. The fluid delivery pen of claim 14, wherein rotational bearings running surface of the thumb pad mate with rotational bearings running surface of the ratchet cap.

16. The fluid delivery pen of claim 13, wherein the clip teeth of the thumb pad are retained within the ratchet cap by the snapping of the clip teeth of the thumb pad on a retention rib of the ratchet cap.

17. The delivery pen of claim 16, wherein the cylindrical axle pin of the thumb pad is provided at a proximal inner surface at the centre of the thumb pad.

18. The fluid delivery pen of claim 17, wherein the cylindrical axle pin of the thumb pad aligns with the ratchet cap.

19. The fluid delivery pen of claim 16, wherein clip teeth of the thumb pad are provided at its inner surface.

20. The fluid delivery pen of claim 13, wherein the cylindrical axle pin of the thumb pad aligns within an axle bore of the ratchet cap.

* * * * *